US009080177B2

(12) United States Patent
Saha

(10) Patent No.: US 9,080,177 B2
(45) Date of Patent: Jul. 14, 2015

(54) PAVEC

(75) Inventor: Deba P. Saha, Nutley, NJ (US)

(73) Assignee: MERCK SHARP & DOHME CORP., Rahway, NJ (US)

( * ) Notice: Subject to any disclaimer, the term of this patent is extended or adjusted under 35 U.S.C. 154(b) by 0 days.

(21) Appl. No.: 14/110,217

(22) PCT Filed: Apr. 2, 2012

(86) PCT No.: PCT/US2012/031785
§ 371 (c)(1), (2), (4) Date: Oct. 7, 2013

(87) PCT Pub. No.: WO2012/138591
PCT Pub. Date: Oct. 11, 2012

(65) Prior Publication Data

US 2014/0030760 A1 Jan. 30, 2014

Related U.S. Application Data

(60) Provisional application No. 61/473,431, filed on Apr. 8, 2011.

(51) Int. Cl.

| | |
|---|---|
| ***C12P 21/06*** | (2006.01) |
| ***C12N 15/63*** | (2006.01) |
| ***C12N 15/70*** | (2006.01) |
| *C07H 21/02* | (2006.01) |
| *C07H 21/04* | (2006.01) |
| *C12N 1/00* | (2006.01) |
| *C12N 5/02* | (2006.01) |
| *C12N 15/00* | (2006.01) |
| *C12N 15/09* | (2006.01) |

(52) U.S. Cl.
CPC ................ *C12N 15/63* (2013.01); *C12N 15/70* (2013.01)

(58) Field of Classification Search
None
See application file for complete search history.

(56) References Cited

U.S. PATENT DOCUMENTS

| | | | |
|---|---|---|---|
| 6,303,308 | B1 | 10/2001 | Halle et al. |
| 2007/0134201 | A1 | 6/2007 | Schleper |

FOREIGN PATENT DOCUMENTS

| | | |
|---|---|---|
| CN | 1938428 | 3/2007 |
| WO | WO2005047512 | 5/2005 |
| WO | WO2010056816 | 5/2010 |

OTHER PUBLICATIONS

Lucas et al., CCTU4881.g1 CCTU *Botryllus schlosseri* total asexual and embronic development subtracted *Botryllus schlosseri* cDNA clone CCTU4881 3', mRNA sequence, Genbank accession No. JG359611, Mar. 22, 2011, 1, US.

Hua et al., cloning and expression of anti human apo b single chain antibody gene, Linchuang shuxue yu jianyan, 2006, 127-128, 2, CN.

Tong, Expression of human anti-HBsAg-interferon fusion protein in CHO cells, Zhonghua ganzangbing zazhi, 2001, 114-116, 2, CN.

*Primary Examiner* — Celine Qian
*Assistant Examiner* — Nancy J Leith

(57) ABSTRACT

This application provides, in part, pAVEC plasmids and methods of use of such plasmids for the production of polypeptides such as immunoglobulins as well as the generation of recombined versions of such plasmids which contain polynucleotides encoding such polypeptides.

11 Claims, 2 Drawing Sheets

PAVEC

This application claims the benefit of U.S. Provisional Patent Application No. 61/473,431, filed Apr. 8, 2011; which is herein incorporated by reference in its entirety.

FIELD OF THE INVENTION

The field of the invention relates to plasmids which may be used, for example, to express polypeptides of interest.

BACKGROUND OF THE INVENTION

Culturing cells for the commercial production of therapeutic proteins is a costly process. The equipment required is expensive and research and development and production costs are high. Development of cell culture processes which maximize the quantity of therapeutic protein produced per liter of cell culture will minimize the resources necessary to produce a given quantity of the protein. It is, thus, desirable to use commercially viable reagents which produce large quantities of proteins.

Many naturally occurring cells do not produce large quantities of desired proteins, under standard culture conditions. Rather, extensive research and development of cell culture processes, which coax cells in culture to generate large quantities of therapeutic protein, must be performed. Typically, identifying plasmid vectors useful for expressing a protein at a high level requires a significant amount of inventive input.

SUMMARY OF THE INVENTION

The present invention provides, in part, an isolated pAVEC plasmid vector which is linear or circular comprising a multiple cloning site comprising the restriction sites:

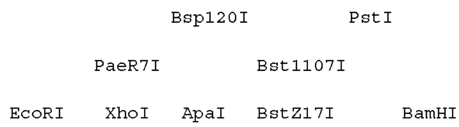

e.g., comprising the nucleotide sequence of SEQ ID NO: 2; for example, the plasmid vector is characterized by the plasmid map of FIG. 1; wherein the plasmid comprises the nucleotide sequence set forth in SEQ ID NO: 1. The pAVEC plasmid vectors may be circular and, thus, capable of autonomous ectopic reproduction in a host cell; or linear and capable of use, e.g., for integration into the chromosomal DNA of a host cell.

The present invention further comprises a method for making a recombined plasmid comprising cleaving a pAVEC plasmid and ligating the ends of the cleaved plasmid to compatible ends of an introduced polynucleotide (e.g., encoding an immunoglobulin such as Abciximab, Adalimumab, Alemtuzumab, Basiliximab, Bevacizumab, Cetuximab, Certolizumab pegol, Dalotuzumab (MK0646), Daclizumab, Denosumab, Eculizumab, Efalizumab, Gemtuzumab, Ibritumomab tiuxetan, Infliximab, Muromonab-CD3, Natalizumab, Omalizumab, Palivizumab, Panitumumab, Ranibizumab, Rituximab, Robatumumab, Tositumomab, ALD518 and Trastuzumab; or, an immunoglobulin chain that is a heavy or light chain of an antibody or antigen-binding fragment thereof that binds specifically to an antigen selected from the group consisting of: VEGF, VEGFR, EGF, EGFR, TNFalpha, TGFbeta, TRAIL-R1, Nav1.7, Nav1.8, ERK, MEK, TRAIL-R2, IL-6, IL-6R, IGF1R, IL-23p19, IL-23R, PCSK9, CD20, RANKL, RANK, CD33, CD11a, ErbB2, IgE, a G-protein coupled receptor (GPCR) an HIV antigen, an HCV antigen and a respiratory syncytial virus (RSV) antigen) such that a closed circular plasmid is produced, e.g., wherein the introduced polynucleotide is operably linked to a promoter in the plasmid, such as the hCMV promoter. Any recombined plasmid produced by such a method forms part of the present invention.

The present invention further includes an isolated host cell (e.g., bacterial or mammalian cell such as a CHO cell) comprising an isolated host cell comprising any of the pAVEC plasmids of the present invention.

The present invention also provides a method for producing a recombinant polypeptide in an isolated host cell, comprising introducing the any recombined pAVEC plasmid vector of the present invention that comprises a polynucleotide that encodes a polypeptide e.g., wherein the polynucleotide encoding the polypeptide is operably linked to a promoter in the plasmid, such as the hCMV promoter; into the host cell under conditions which allow for expression of the polypeptide; and optionally, purifying the polypeptide.

Furthermore, the present invention includes a kit comprising a pAVEC plasmid vector of the invention and one or more additional components.

DETAILED DESCRIPTION OF THE INVENTION

The present invention provides an expression vector useful for recombinant protein expression in any cell, for example in a mammalian cell, a bacterial cell, a yeast cell or an insect cell. The vector may be used to transiently or stably express a broad range of recombinant proteins. The multiple cloning site of the vector offers many common and rare restriction sites to accommodate a variety of expression cassettes.

Figure 1:
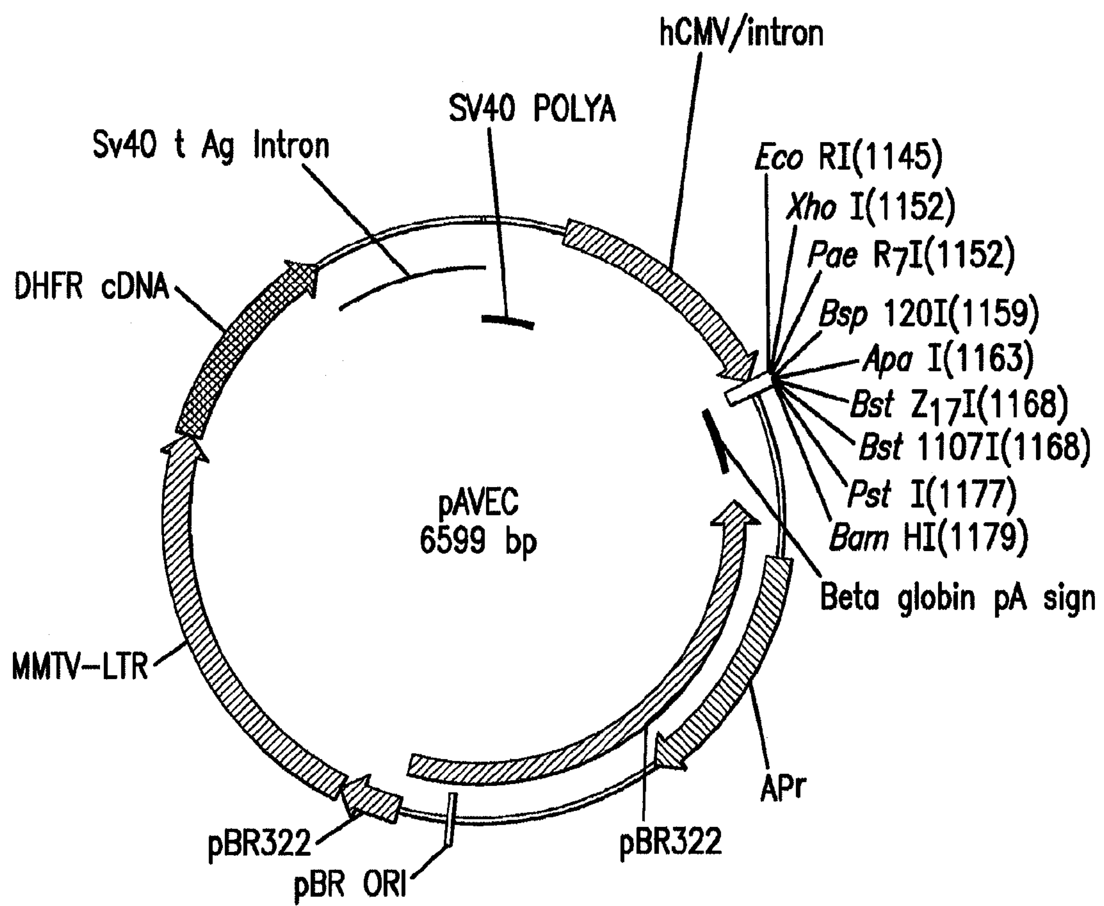
FIG. 1: pAVEC plasmid map.

A pAVEC plasmid is a plasmid characterized by the plasmid map set forth in FIG. 1 and/or comprising or consisting of the nucleotide sequence of SEQ ID NO: 1; the term also encompasses a recombined plasmid produced by a process comprising cleaving pAVEC plasmid and ligating the ends of the cleaved plasmid to compatible ends of an introduced polynucleotide such that a closed circular plasmid is produced which comprises the introduced polynucleotide.

Molecular Biology

In accordance with the present invention there may be employed conventional molecular biology, microbiology, and recombinant DNA techniques within the skill of the art. Such techniques are explained in the literature. See, e.g., Sambrook, Fritsch & Maniatis, *Molecular Cloning: A Laboratory Manual*, Second Edition (1989) Cold Spring Harbor Laboratory Press, Cold Spring Harbor, N.Y. (herein "Sambrook, et al., 1989"); *DNA Cloning: A Practical Approach*, Volumes I and II (D. N. Glover ed. 1985); *Oligonucleotide Synthesis* (M. J. Gait ed. 1984); *Nucleic Acid Hybridization* (B. D. Hames & S. J. Higgins eds. (1985)); *Transcription And Translation* (B. D. Hames & S. J. Higgins, eds. (1984)); *Animal Cell Culture* (R. I. Freshney, ed. (1986)); *Immobilized Cells And Enzymes* (IRL Press, (1986)); B. Perbal, *A Practi-*

*cal Guide To Molecular Cloning* (1984); F. M. Ausubel, et al. (eds.), *Current Protocols in Molecular Biology*, John Wiley & Sons, Inc. (1994).

A "polynucleotide," "nucleic acid" or "nucleic acid molecule" includes DNA or RNA. For example, in an embodiment of the invention, the polynucleotide is the circular plasmid pAVEC.

A "polynucleotide sequence," "nucleic acid sequence" or "nucleotide sequence" is a series of nucleotides in a nucleic acid, such as DNA or RNA, and means any chain of two or more nucleotides.

A "coding sequence" or a sequence "encoding" an expression product such as a RNA or peptide (e.g., an immunoglobulin chain), is a nucleotide sequence that, when expressed, results in production of the product.

As used herein, the term "oligonucleotide" refers to a nucleic acid, generally of no more than about 300 nucleotides (e.g., 30, 40, 50, 60, 70, 80, 90, 150, 175, 200, 250 or 300), that may be hybridizable to a genomic DNA molecule, a cDNA molecule, or an mRNA molecule encoding a gene, mRNA, cDNA, or other nucleic acid of interest. Oligonucleotides are usually single-stranded, but may be double-stranded. Oligonucleotides can be labeled, e.g., by incorporation of $^{32}$P-nucleotides, $^{3}$H-nucleotides, $^{14}$C-nucleotides, $^{35}$S-nucleotides or nucleotides to which a label, such as biotin, has been covalently conjugated. In one embodiment, a labeled oligonucleotide can be used as a probe to detect the presence of a nucleic acid. In another embodiment, oligonucleotides (one or both of which may be labeled) can be used as PCR primers, either for cloning full length or a fragment of the gene, or to detect the presence of nucleic acids. Generally, oligonucleotides are prepared synthetically, e.g., on a nucleic acid synthesizer.

A "protein sequence," "peptide sequence" or "polypeptide sequence," or "amino acid sequence" refers to a series of two or more amino acids in a protein, peptide or polypeptide.

"Protein," "peptide" or "polypeptide" includes a contiguous string of two or more amino acids.

The term "isolated polynucleotide" or "isolated polypeptide" includes a polynucleotide (e.g., RNA or DNA molecule, or a mixed polymer) or a polypeptide, respectively, which is partially or fully separated from other components that are normally found in cells or in recombinant DNA expression systems or any other contaminant. These components include, but are not limited to, cell membranes, cell walls, ribosomes, polymerases, serum components and extraneous genomic sequences.

An isolated polynucleotide (e.g., pAVEC) or polypeptide will, preferably, be an essentially homogeneous composition of molecules but may contain some heterogeneity.

The term "host cell" includes any cell of any organism that is selected, modified, transfected, transformed, grown, or used or manipulated in any way, for the production of a substance by the cell, for example the expression or replication, by the cell, of a gene, a polynucleotide such as a circular plasmid (e.g., pAVEC) or RNA or a protein. For example, a host cell may be a mammalian cell or bacterial cell (e.g., *E. coli*) or any isolated cell capable of maintaining pAVEC plasmid and, in an embodiment of the invention, promoting expression of a polypeptide encoded by a polynucleotide in the plasmid, e.g., an immunoglobulin chain. Examples of mammalian host cells include, by way of nonlimiting example, Chinese hamster ovary (CHO) cells, CHO-K1 cells, CHO-DXB-11 cells, CHO-DG44 cells, bovine mammary epithelial cells, mouse Sertoli cells, canine kidney cells, buffalo rat liver cells, human lung cells, mouse mammary tumor cells, rat fibroblasts, bovine kidney (MDBK) cells, NSO cells, SP2 cells, TRI cells, MRC 5 cells, FS4 cells, HEK-293T cells, NIH-3T3 cells, HeLa cells, baby hamster kidney (BHK) cells, African green monkey kidney (COS) cells, human hepatocellular carcinoma (e.g., Hep G2) cells, A549 cells, etc. In one embodiment, the mammalian host cell is a human host cell. Mammalian host cells can be cultured according to methods known in the art (see, e.g., J. Immunol. Methods 56:221 (1983), *Animal Cell Culture: A Practical Approach* 2nd *Ed*., Rickwood, D. and Hames, B. D., eds. Oxford University Press, New York (1992)). Examples of suitable *E. coli* include DH1, DH5, DH5alpha, XL1-Blue, SURE, SCS110, OneShot Top 10, and HB101. In an embodiment of the invention an pAVEC plasmid of the present invention is maintained ectopically in a host cell and/or integrated into chromosomal DNA of the host cell. Such host cells and methods of use thereof, e.g., as discussed herein, form part of the present invention.

Vectors of the invention, such as pAVEC, may be introduced into host cells according to any of the many techniques known in the art, e.g., dextran-mediated transfection, polybrene-mediated transfection, protoplast fusion, electoporation, calcium phosphate co-precipitation, lipofection, direct microinjection of the vector into nuclei, or any other means appropriate for a given host cell type.

A "cassette" or an "expression cassette" refers to a DNA coding sequence or segment of DNA that codes for an expression product (e.g., peptide or RNA) that can be inserted into a vector, e.g., at defined restriction sites. The expression cassette may comprise a promoter and/or a terminator and/or polyA signal operably linked to the DNA coding sequence.

In general, a "promoter" or "promoter sequence" is a DNA regulatory region capable of binding an RNA polymerase in a cell (e.g., directly or through other promoter-bound proteins or substances) and initiating transcription of a coding sequence. A promoter sequence is, in general, bounded at its 3' terminus by the transcription initiation site and extends upstream (5' direction) to include the minimum number of bases or elements necessary to initiate transcription at any level. Within the promoter sequence may be found a transcription initiation site (conveniently defined, for example, by mapping with nuclease S1), as well as protein binding domains (consensus sequences) responsible for the binding of RNA polymerase. The promoter may be operably associated with or operably linked to other expression control sequences, including enhancer and repressor sequences or with a nucleic acid to be expressed. An expression control sequence is operably associated with or operably linked to a promoter if it regulates expression from said promoter.

Promoters which may be used to control gene expression include, but are not limited to, SRα promoter (Takebe et al., Molec. and Cell. Bio. 8:466-472 (1988)), the human CMV immediate early promoter (Boshart et al., Cell 41:521-530 (1985); Foecking et al., Gene 45:101-105 (1986)), the mouse CMV immediate early promoter, the SV40 early promoter region (Benoist et al., Nature 290:304-310 (1981)), the *Orgyia pseudotsugata* immediate early promoter, the herpes thymidine kinase promoter (Wagner et al., Proc. Natl. Acad. Sci. USA 78:1441-1445 (1981)), the regulatory sequences of the metallothionein gene (Brinster et al., Nature 296:39-42 (1982)); prokaryotic expression vectors such as the β-lactamase promoter (Villa-Komaroff et al., Proc. Natl. Acad. Sci. USA 75:3727-3731 (1978)), or the tac promoter (DeBoer et al., Proc. Natl. Acad. Sci. USA 80:21-25 (1983)); and promoter elements from yeast or other fungi such as the GAL1, GAL4 or GAL10 promoter, the ADH (alcohol dehydrogenase) promoter, PGK (phosphoglycerol kinase) promoter or the alkaline phosphatase promoter.

Viral long terminal repeat promoters such as the mouse mammary tumor virus long terminal repeat (MMTV-LTR) (Fasel et al., EMBO J. 1(1):3-7 (1982)), the moloney murine sarcoma virus long terminal repeat (Reddy et al., Proc. Natl. Acad. Sci. USA 77(9): 5234-5238 (1980)), the moloney murine leukemia virus long terminal repeat (Van Beveren et al., Proc. Natl. Acad. Sci. USA 77(6): 3307-3311 (1980)), the HIV LTR (Genbank Accession No. AB100245), the bovine foamy virus LTR (Genbank Accession No. NC_001831), RSV 5'-LTR (Genbank Accession No. K00087), the HIV-2 LTR (Genbank Accession No. NC_001722), an avian retroviral LTR (Ju et al., Cell 22: 379-386 (1980)) and the human herpesvirus LTR (Genbank Accession No. NC_001806) may be included in the vectors of the present invention.

Other acceptable promoters include the human CMV5 promoter, the murine CMV promoter, the EF1α promoter, the SV40 promoter, a hybrid CMV promoter for liver specific expression (e.g., made by conjugating CMV immediate early promoter with the transcriptional promoter elements of either human α1-antitrypsin (HAT) or albumin (HAL) promoter), or promoters for hepatoma specific expression (e.g., wherein the transcriptional promoter elements of either human albumin (HAL; about 1000 bp) or human α1-antitrypsin (HAT, about 2000 bp) are combined with a 145 bp long enhancer element of human α1-microglobulin and bikunin precursor gene (AMBP); HAL-AMBP and HAT-AMBP).

In addition, bacterial promoters, such as the T7 RNA Polymerase promoter or the tac promoter, may be used to control expression.

In one embodiment, the promoter is the human CMV (hCMV) promoter. The hCMV promoter provides a high level of expression in a variety of mammalian cell types.

A coding sequence is "under the control of", "functionally associated with", "operably linked to" or "operably associated with" transcriptional and translational control sequences in a cell when the sequences direct or regulate expression of the sequence. For example, a promoter operably linked to a gene will direct RNA polymerase mediated transcription of the coding sequence into RNA, preferably mRNA, which may then be spliced (if it contains introns) and, optionally, translated into a protein encoded by the coding sequence. A terminator/polyA signal operably linked to a gene terminates transcription of the gene into RNA and directs addition of a polyA signal onto the RNA.

The terms "express" and "expression" mean allowing or causing the information in a gene, RNA or DNA sequence to become manifest; for example, producing a protein by activating the cellular functions involved in transcription and translation of a corresponding gene. "Express" and "expression" include transcription of DNA to RNA and of RNA to protein. A DNA sequence is expressed in or by a cell to form an "expression product" such as an RNA (e.g., mRNA) or a protein. The expression product itself may also be said to be "expressed" by the cell.

The term "transformation" means the introduction of a nucleic acid into a cell. The introduced gene or sequence may be called a "clone". A host cell that receives the introduced DNA or RNA has been "transformed" and is a "transformant" or a "clone." The DNA or RNA introduced to a host cell can come from any source, including cells of the same genus or species as the host cell, or from cells of a different genus or species. Examples of transformation methods which are very well known in the art include liposome delivery, electroporation, $CaPO_4$ transformation, DEAE-Dextran transformation, microinjection and viral infection.

The present invention includes vectors which comprise polynucleotides of the invention. The term "vector" may refer to a vehicle (e.g., a plasmid) by which a DNA or RNA sequence can be introduced into a host cell, so as to transform the host and, optionally, promote expression and/or replication of the introduced sequence.

The polynucleotides of the invention may be expressed in an expression system. The term "expression system" means a host cell and compatible vector which, under suitable conditions, can express a protein or nucleic acid which is carried by the vector and introduced to the host cell. Common expression systems include *E. coli* host cells and plasmid vectors, insect host cells and baculovirus vectors, and mammalian host cells and vectors such as plasmids, cosmids, BACs, YACs and viruses such as adenovirus and adenovirus associated virus (AAV).

Vectors

The invention provides the a plasmid which comprises the following multiple cloning site:

EcoRI, XhoI, PaeR7I, Bs120I, BstZ17I, Bst1107I, PstI, BamH1, e.g., comprising the relative spacing between these restriction sites as indicated in FIG. 1, e.g., wherein overlapping restriction sites with the multiple cloning site is characterized as follows:

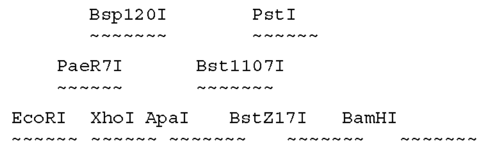

In an embodiment of the invention, the multiple cloning site comprises the nucleotide sequence:

(SEQ ID NO: 1)
GAATTCTCTC GAGTGGGCCC AGTATACACT GCAGGGATCC

In the embodiment of the invention, the pAVEC plasmid of the present invention is characterized by the plasmid map set forth in FIG. 1.

In an embodiment of the invention, the plasmid is pAVEC which comprises the following nucleotide sequence:

(SEQ ID NO: 2)
1 CTTGACTAGA GATCATAATC AGCCATACCA CATTTGTAGA GGTTTTACTT GCTTTAAAAA

61 ACCTCCCACA CCTCCCCCTG AACCTGAAAC ATAAAATGAA TGCAATTGTT GTTGTTAACT

121 TGTTTATTGC AGCTTATAAT GGTTACAAAT AAAGCAATAG CATCACAAAT TTCACAAATA

181 AAGCATTTTT TTCACTGCAT TCTAGTTGTG GTTTGTCCAA ACTCATCAAT GTATCTTATC

241 ATGTCTGGAT CGATCCAAGC TTCGAGCACC GGTGGCCCGG GCCGGTCCGA CTAGTTACGA

301 TGTACGGGCC AGATATACGC GTTGACATTG ATTATTGACT AGTTATTAAT AGTAATCAAT

361 TACGGGGTCA TTAGTTCATA GCCCATATAT GGAGTTCCGC GTTACATAAC TTACGGTAAA

421 TGGCCCGCCT GGCTGACCGC CCAACGACCC CCGCCCATTG ACGTCAATAA TGACGTATGT

-continued

```
481   TCCCATAGTA ACGCCAATAG GGACTTTCCA TTGACGTCAA
      TGGGTGGAGT ATTTACGGTA

541   AACTGCCCAC TTGGCAGTAC ATCAAGTGTA TCATATGCCA
      AGTACGCCCC CTATTGACGT

601   CAATGACGGT AAATGGCCCG CCTGGCATTA TGCCCAGTAC
      ATGACCTTAT GGGACTTTCC

661   TACTTGGCAG TACATCTACG TATTAGTCAT CGCTATTACC
      ATGGTGATGC GGTTTTGGCA

721   GTACATCAAT GGGCGTGGAT AGCGGTTTGA CTCACGGGGA
      TTTCCAAGTC TCCACCCCAT

781   TGACGTCAAT GGGAGTTTGT TTTGGCACCA AAATCAACGG
      GACTTTCCAA AATGTCGTAA

841   CAACTCCGCC CCATTGACGC AAATGGGCGG TAGGCGTGTA
      CGGTGGGAGG TCTATATAAG

901   CAGAGCTCTC TGGCTAACTA GAGAACCCAC TGCTTACTGG
      CTTATCGAAA TTAATACGAC

961   TCACTATAGC AATTGCACGT GTGGCCACAG GTAAGTTTAA
      AGCTCAGGTC GAGACCGGGC

1021  CTTTGTCCGG CGCTCCCTTG GAGCCTACCT AGACTCAGCC
      GGCTCTCCAC GCTTTGCCTG

1081  ACCCTGCTTG CTCAACTCTA CGTCTTTGTT TCGTTTTCTG
      TTCCTTTCTC TCCACAGGCT

1141  TAAGAATTCT CTCGAGTGGG CCCAGTATAC ACTGCAGGGA
      TCCAGATCCC CCTCGCTTTC

1201  TTGCTGTCCA ATTTCTATTA AAGGTTCCTT TGTTCCCTAA
      GTCCAACTAC TAAACTGGGG

1261  GATATTATGA AGGGCCTTGA GCATCTGGAT TCTGCCTAAT
      AAAAAACATT TATTTTCATT

1321  GCAATGATGT ATTTAAATTA TTTCTGAATA TTTTACTAAA
      AAGGGAATGT GGGAGGTCAG

1381  TGCATTTAAA ACATAAAGAA ATGAAGAGGG GGATCTGTCG
      ACAAGCTCTA GAGAGCTCCA

1441  TATGTGGCCA TCGCGATTAA TTAATCGCGA GCGGCCGCCA
      TATGTGGCCA ACGCGTGGTA

1501  CCGGCCGGCC GCGCGCTGTA CATCCGGATG ATCAGCTGAG
      GGTTTAAACG GCGCGCCTCT

1561  AGACAATTCT TGAAGACGAA AGGGCCTCGT GATACGCCTA
      TTTTTATAGG TTAATGTCAT

1621  GATAATAATG GTTTCTTAGA CGTCAGGTGG CACTTTTCGG
      GGAAATGTGC GCGGAACCCC

1681  TATTTGTTTA TTTTTCTAAA TACATTCAAA TATGTATCCG
      CTCATGAGAC AATAACCCTG

1741  ATAAATGCTT CAATAATATT GAAAAAGGAA GAGTATGAGT
      ATTCAACATT TCCGTGTCGC

1801  CCTTATTCCC TTTTTTGCGG CATTTTGCCT TCCTGTTTTT
      GCTCACCCAG AAACGCTGGT

1861  GAAAGTAAAA GATGCTGAAG ATCAGTTGGG TGCACGAGTG
      GGTTACATCG AACTGGATCT

1921  CAACAGCGGT AAGATCCTTG AGAGTTTTCG CCCCGAAGAA
      CGTTTTCCAA TGATGAGCAC

1981  TTTTAAAGTT CTGCTATGTG GCGCGGTATT ATCCCGTGTT
      GACGCCGGGC AAGAGCAACT

2041  CGGTCGCCGC ATACACTATT CTCAGAATGA CTTGGTTGAG
      TACTCACCAG TCACAGAAAA
```

-continued

```
2101  GCATCTTACG GATGGCATGA CAGTAAGAGA ATTATGCAGT
      GCTGCCATAA CCATGAGTGA

2161  TAACACTGCG GCCAACTTAC TTCTGACAAC GATCGGAGGA
      CCGAAGGAGC TAACCGCTTT

2221  TTTGCACAAC ATGGGGGATC ATGTAACTCG CCTTGATCGT
      TGGGAACCGG AGCTGAATGA

2281  AGCCATACCA AACGACGAGC GTGACACCAC GATGCCTGTA
      GCAATGGCAA CAACGTTGCG

2341  CAAACTATTA ACTGGCGAAC TACTTACTCT AGCTTCCCGG
      CAACAATTAA TAGACTGGAT

2401  GGAGGCGGAT AAAGTTGCAG GACCACTTCT GCGCTCGGCC
      CTTCCGGCTG GCTGGTTTAT

2461  TGCTGATAAA TCTGGAGCCG GTGAGCGTGG GTCTCGCGGT
      ATCATTGCAG CACTGGGGCC

2521  AGATGGTAAG CCCTCCCGTA TCGTAGTTAT CTACACGACG
      GGGAGTCAGG CAACTATGGA

2581  TGAACGAAAT AGACAGATCG CTGAGATAGG TGCCTCACTG
      ATTAAGCATT GGTAACTGTC

2641  AGACCAAGTT TACTCATATA TACTTTAGAT TGATTTAAAA
      CTTCATTTTT AATTTAAAAG

2701  GATCTAGGTG AAGATCCTTT TTGATAATCT CATGACCAAA
      ATCCCTTAAC GTGAGTTTTC

2761  GTTCCACTGA GCGTCAGACC CCGTAGAAAA GATCAAAGGA
      TCTTCTTGAG ATCCTTTTTT

2821  TCTGCGCGTA ATCTGCTGCT TGCAAACAAA AAAACCACCG
      CTACCAGCGG TGGTTTGTTT

2881  GCCGGATCAA GAGCTACCAA CTCTTTTTCC GAAGGTAACT
      GGCTTCAGCA GAGCGCAGAT

2941  ACCAAATACT GTCCTTCTAG TGTAGCCGTA GTTAGGCCAC
      CACTTCAAGA ACTCTGTAGC

3001  ACCGCCTACA TACCTCGCTC TGCTAATCCT GTTACCAGTG
      GCTGCTGCCA GTGGCGATAA

3061  GTCGTGTCTT ACCGGGTTGG ACTCAAGACG ATAGTTACCG
      GATAAGGCGC AGCGGTCGGG

3121  CTGAACGGGG GGTTCGTGCA CACAGCCCAG CTTGGAGCGA
      ACGACCTACA CCGAACTGAG

3181  ATACCTACAG CGTGAGCTAT GAGAAAGCGC CACGCTTCCC
      GAAGGGAGAA AGGCGGACAG

3241  GTATCCGGTA AGCGGCAGGG TCGGAACAGG AGAGCGCACG
      AGGGAGCTTC CAGGGGGAAA

3301  CGCCTGGTAT CTTTATAGTC CTGTCGGGTT TCGCCACCTC
      TGACTTGAGC GTCGATTTTT

3361  GTGATGCTCG TCAGGGGGGC GGAGCCTATG GAAAAACGCC
      AGCAACGCGG CCTTTTTACG

3421  GTTCCTGGCC TTTTGCTGGC CTTTTGCTCA CATGTTCTTT
      CCTGCGTTAT CCCCTGATTC

3481  TGTGGATAAC CGTATTACCG CCTTTGAGTG AGCTGATACC
      GCTCGCCGCA GCCGAACGAC

3541  CGAGCGCAGC GAGTCAGTGA GCGAGGAAGC GGAAGAGCGC
      TAGCAGCACG CCATAGTGAC

3601  TGGCGATGCT GTCGGAATGG ACGATATCCC GCAAGAGGCC
      CGGCAGTACC GGCATAACCA

3661  AGCCTATGCC TACAGCATCC AGGGTGACGG TGCCGAGGAT
      GACGATGAGC GCATTGTTAG
```

-continued

```
3721  ATTTCATACA CGGTGCCTGA CTGCGTTAGC AATTTAACTG
      TGATAAACTA CCGCATTAAA

3781  GCTCAGATCT GAGCTTGGGC AGAAATGGTT GAACTCCCGA
      GAGTGTCCTA CACCTAGGGG

3841  AGAAGCAGCC AAGGGGTTGT TTCCCACCAA GGACGACCCG
      TCTGCGCACA AACGGATGAG

3901  CCCATCAGAC AAAGACATAT TCATTCTCTG CTGCAAACTT
      GGCATAGCTC TGCTTTGCCT

3961  GGGGCTATTG GGGGAAGTTG CGGTTCGTGC TCGCAGGGCT
      CTCACCCTTG ACTCTTTTAA

4021  TAGCTCTTCT GTGCAAGATT ACAATCTAAA CAATTCGGAG
      AACTCGACCT TCCTCCTGAG

4081  GCAAGGACCA CAGCCAACTT CCTCTTACAA GCCGCATCGA
      TTTTGTCCTT CAGAAATAGA

4141  AATAAGAATG CTTGCTAAAA ATTATATTTT TACCAATAAG
      ACCAATCCAA TAGGTAGATT

4201  ATTAGTTACT ATGTTAAGAA ATGAATCATT ATCTTTTAGT
      ACTATTTTTA CTCAAATTCA

4261  GAAGTTAGAA ATGGGAATAG AAAATAGAAA GAGACGCTCA
      ACCTCAATTG AAGAACAGGT

4321  GCAAGGACTA TTGACCACAG GCCTAGAAGT AAAAAAGGGA
      AAAAAGAGTG TTTTTGTCAA

4381  AATAGGAGAC AGGTGGTGGC AACCAGGGAC TTATAGGGGA
      CCTTACATCT ACAGACCAAC

4441  AGATGCCCCC TTACCATATA CAGGAAGATA TGACTTAAAT
      TGGGATAGGT GGGTTACAGT

4501  CAATGGCTAT AAAGTGTTAT ATAGATCCCT CCCTTTTCGT
      GAAAGACTCG CCAGAGCTAG

4561  ACCTCCTTGG TGTATGTTGT CTCAAGAAGA AAAAGACGAC
      ATGAAACAAC AGGTACATGA

4621  TTATATTTAT CTAGGAACAG GAATGCACTT TTGGGGAAAG
      ATTTTCCATA CCAAGGAGGG

4681  GACAGTGGCT GGACTAATAG AACATTATTC TGCAAAAACT
      CATGGCATGA GTTATTATGA

4741  ATAGCCTTTA TTGGCCCAAC CTTGCGGTTC CCAGGGCTTA
      AGTAAGTTTT TGGTTACAAA

4801  CTGTTCTTAA AACGAGGATG TGAGACAAGT GGTTTCCTGA
      CTTGGTTTGG TATCAAAGGT

4861  TCTGATCTGA GCTCTGAGTG TTCTATTTTC CTATGTTCTT
      TTGGAATTTA TCCAAATCTT

4921  ATGTAAATGC TTATGTAAAC CAAGATATAA AAGAGTGCTG
      ATTTTTTGAG TAAACTTGCA

4981  ACAGTCCTAA CATTCACCTC TTGTGTGTTT GTGTCTGTTC
      GCCATCCCGT CTCCGCTCGT

5041  CACTTATCCT TCACTTTCCA GAGGGTCCCC CCGCAGACCC
      CGGCGACCCT CAGGTCGGCC

5101  GACTGCGGCA GCTGGCGCCC GAACAGGGAC CCTCGGATAA
      GTGACCCTTG TCTCTATTTC

5161  TACTATTTGG TGTTTGTCTT GTATTGTCTC TTTCTTGTCT
      GGCTATCATC ACAAGAGCGG

5221  AACGGACTCA CCATAGGGAC CAAGCTCAGA TCTGAGCTTG
      GGGGGGGGGA CAGCTCAGGG

5281  CTGCGATTTC GCGCCAAACT TGACGGCAAT CCTAGCGTGA
      AGGCTGGTAG GATTTTATCC
```

-continued

```
5341  CCGCTGCCAT CATGGTTCGA CCATTGAACT GCATCGTCGC
      CGTGTCCCAA AATATGGGGA

5401  TTGGCAAGAA CGGAGACCTA CCCTGGCCTC CGCTCAGGAA
      CGAGTTCAAG TACTTCCAAA

5461  GAATGACCAC AACCTCTTCA GTGGAAGGTA AACAGAATCT
      GGTGATTATG GGTAGGAAAA

5521  CCTGGTTCTC CATTCCTGAG AAGAATCGAC CTTTAAAGGA
      CAGAATTAAT ATAGTTCTCA

5581  GTAGAGAACT CAAAGAACCA CCACGAGGAG CTCATTTTCT
      TGCCAAAAGT TTGGATGATG

5641  CCTTAAGACT TATTGAACAA CCGGAATTGG CAAGTAAAGT
      AGACATGGTT TGGATAGTCG

5701  GAGGCAGTTC TGTTTACCAG GAAGCCATGA ATCAACCAGG
      CCACCTCAGA CTCTTTGTGA

5761  CAAGGATCAT GCAGGAATTT GAAAGTGACA CGTTTTTCCC
      AGAAATTGAT TTGGGGAAAT

5821  ATAAACTTCT CCCAGAATAC CCAGGCGTCC TCTCTGAGGT
      CCAGGAGGAA AAAGGCATCA

5881  AGTATAAGTT TGAAGTCTAC GAGAAGAAAG ACTAACAGGA
      AGATGCTTTC AAGTTCTCTG

5941  CTCCCCTCCT AAAGCTATGC ATTTTTATAA GACCATGGGA
      CTTTTGCTGG CTTTAGATCG

6001  ATCTTTGTGA AGGAACCTTA CTTCTGTGGT GTGACATAAT
      TGGACAAACT ACCTACAGAG

6061  ATTTAAAGCT CTAAGGTAAA TATAAAATTT TTAAGTGTAT
      AATGTGTTAA ACTACTGATT

6121  CTAATTGTTT GTGTATTTTA GATTCCAACC TATGGAACTG
      ATGAATGGGA GCAGTGGTGG

6181  AATGCCTTTA ATGAGGAAAA CCTGTTTTGC TCAGAAGAAA
      TGCCATCTAG TGATGATGAG

6241  GCTACTGCTG ACTCTCAACA TTCTACTCCT CCAAAAAAGA
      AGAGAAAGGT AGAAGACCCC

6301  AAGGACTTTC CTTCAGAATT GCTAAGTTTT TTGAGTCATG
      CTGTGTTTAG TAATAGAACT

6361  CTTGCTTGCT TTGCTATTTA CACCACAAAG GAAAAAGCTG
      CACTGCTATA CAAGAAAATT

6421  ATGGAAAAAT ATTCTGTAAC CTTTATAAGT AGGCATAACA
      GTTATAATCA TAACATACTG

6481  TTTTTTCTTA CTCCACACAG GCATAGAGTG TCTGCTATTA
      ATAACTATGC TCAAAAATTG

6541  TGTACCTTTA GCTTTTTAAT TTGTAAAGGG GTTAATAAGG
      AATATTTGAT GTATAGTGC
```

Genes

Any of several genes may be inserted into the plasmids of the present invention, for example, immunoglobulins. Plasmids of the present invention encoding any of the following target immunoglobulin amino acid sequences form part of the present invention. The present invention encompasses the product of any method wherein a polynucleotide or gene (e.g., encoding an immunoglobulin) is inserted into pAVEC and which, in the process, results in a loss of some pAVEC polynucleotide sequence, e.g., due to excision of a portion of the multiple cloning site so as to generate restriction enzymatically cleaved sites that are compatible for ligation of the introduced gene into the vector. The product of such a method may be referred to herein as a pAVEC vector that comprises a particular gene or polynucleotide.

The scope of the present invention includes a method for introducing a polynucleotide into the pAVEC plasmid comprising cleaving the plasmid, e.g., with one or more restriction endonucleases, e.g., in the plasmid multiple cloning site, and ligating the ends of the cleaved plasmid to the compatible ends of the introduced polynucleotide, e.g., with a DNA ligase to produce a closed recombined plasmid. Any recombined plasmid that is the product of such a method is part of the present invention. Compatible ends of polynucleotides are ends that can be joined together by a DNA ligase. In an embodiment of the invention, the ends are blunt or sticky ends, e.g., the result of cleavage by a restriction endonuclease such as EcoR1 or BamH1.

In an embodiment of the invention, the immunoglobulin is the mature or unprocessed version of any of the following polypeptides, e.g., the variable region only or the variable domain and the constant domain:

19D12/15H12 Light Chain (SEQ ID NO: 3)

```
MSPSQLIGFLLLWVPASRGEIVLTQVPDFQSVTPKEKVTITCRASQSIGSSLHWYQQKPD
QSPKLLIKYASQSLSGVPSRFSGSGSGTDFTLTINSLEAEDAAAYYCHQSSRLPHTFGGG
TKVEIKRT
```

19D12/15H12 Heavy Chain (SEQ ID NO: 4)

```
MEFGLSWVFLVAILKGVQCEVQLVQSGGGLVHPGGSLRLSCAASGFTFSSFAMHWVRQAP
GKGLEWISVIDTRGATYYADSVKGRFTISRDNAKNSLYLQMNSLRAEDMAVYYCARLGNF
YYGMDVWGQGTTVTVSS
```

19D12/15H12 Light Chain-C (LCC)

(SEQ ID NO: 5)

```
M S P S Q L I G F L L L W V P A S
R G E I V L T Q S P D S L S V T P
G E R V T I T C R A S Q S I G S S
L H W Y Q Q K P G Q S P K L L I K
Y A S Q S L S G V P S R F S G S G
S G T D F T L T I S S L E A E D A
A A Y Y C H Q S S R L P H T F G Q
G T K V E I K R T
```

19D12/15H12 Light Chain-D (LCD)

(SEQ ID NO: 6)

```
M S P S Q L I G F L L L W V P A S
R G E I V L T Q S P D S L S V T P
G E R V T I T C R A S Q S I G S S
L H W Y Q Q K P G Q S P K L L I K
Y A S Q S L S G V P S R F S G S G
S G T D F T L T I S S L E A E D A
A v Y Y C H Q S S R L P H T F G Q
G T K V E I K R T
```

19D12/15H12 Light Chain-E (LCE)

(SEQ ID NO: 7)

```
M S P S Q L I G F L L L W V P A S
R G E I V L T Q S P D S L S V S P
G E R A T L S C R A S Q S I G S S
L H W Y Q Q K P G Q A P R L L I K
Y A S Q S L S G I P D R F S G S G
S G T D F T L T I S R L E P E D A
A A Y Y C H Q S S R L P H T F G Q
G T K V E I K R T
```

19D12/15H12 Light Chain-F (LCF)

(SEQ ID NO: 8)

```
M S P S Q L I G F L L L W V P A S
R G E I V L T Q S P D S L S V S P
G E R A T L S C R A S Q S I G S S
L H W Y Q Q K P G Q A P R L L I K
Y A S Q S L S G I P D R F S G S G
S G T D F T L T I S R L E P E D A
A v Y Y C H Q S S R L P H T F G Q
G T K V E I K R T
```

19D12/15H12 heavy chain-A (HCA)

(SEQ ID NO: 9)

```
Met Glu Phe Gly Leu Ser Trp Val Phe Leu Val Ala Ile Leu Lys Gly Val
Gln Cys Glu Val Gln Leu Val Gln Ser Gly Gly Gly Leu Val Lys Pro Gly
Gly Ser Leu Arg Leu Ser Cys Ala Ala Ser Gly Phe Thr Phe Ser Ser Phe
Ala Met His Trp Val Arg Gln Ala Pro Gly Lys Gly Leu Glu Trp Ile Ser
Val Ile Asp Thr Arg Gly Ala Thr Tyr Tyr Ala Asp Ser Val Lys Gly Arg
Phe Thr Ile Ser Arg Asp Asn Ala Lys Asn Ser Leu Tyr Leu Gln Met Asn
Ser Leu Arg Ala Glu Asp Thr Ala Val Tyr Tyr Cys Ala Arg Leu Gly Asn
Phe Tyr Tyr Gly Met Asp Val Trp Gly Gln Gly Thr Thr Val Thr Val Ser
Ser
```

-continued

19D12/15H12 heavy chain-B (HCB)

(SEQ ID NO: 10)

```
Met Glu Phe Gly Leu Ser Trp Val Phe Leu Val Ala Ile Leu Lys Gly Val
Gln Cys Glu Val Gln Leu Val Gln Ser Gly Gly Gly Leu Val Lys Pro Gly
Gly Ser Leu Arg Leu Ser Cys Ala Ala Ser Gly Phe Thr Phe Ser Ser Phe
Ala Met His Trp Val Arg Gln Ala Pro Gly Lys Gly Leu Glu Trp Ile Ser
Val Ile Asp Thr Arg Gly Ala Thr Tyr Tyr Ala Asp Ser Val Lys Gly Arg
Phe Thr Ile Ser Arg Asp Asn Ala Lys Asn Ser Leu Tyr Leu Gln Met Asn
Ser Leu Arg Ala Glu Asp Thr Ala Val Tyr Tyr Cys Ala Arg Leu Gly Asn
Phe Tyr Tyr Gly Met Asp Val Trp Gly Gln Gly Thr Thr Val Thr Val Ser
Ser
```

See international application publication no. WO2003/100008 which is incorporated herein by reference in its entirety.

Embodiments of the invention include those wherein the plasmid includes more than one immunoglobulin, for example, a combination of any of those set forth herein (e.g., heavy chain Ig. #1.0 and light chain Ig. #1.0, or LCC and HCA; or LCF and HCA; or LCC and HCB).

In an embodiment of the invention the pAVEC plasmid contains a light chain immunoglobulin comprising the amino acid sequence:

(SEQ ID NO: 11)

```
1    DIVMTQSPLS LPVTPGEPAS ISCRSSQSIV HSNGNTYLQW
     YLQKPGQSPQ
51   LLIYKVSNRL YGVPDRFSGS GSGTDFTLKI SRVEAEDVGV
     YYCFQGSHVP
101  WTFGQGTKVE IKRTVAAPSV FIFPPSDEQL KSGTASVVCL
     LNNFYPREAK
151  VQWKVDNALQ SGNSQESVTE QDSKDSTYSL SSTLTLSKAD
     YEKHKVYACE
201  VTHQGLSSPV TKSFNRGEC;
```

and/or, a heavy chain immunoglobulin comprising the amino acid sequence:

(SEQ ID NO: 12);

```
1    QVQLQESGPG LVKPSETLSL TCTVSGYSIT GGYLWNWIRQ
     PPGKGLEWIG
51   YISYDGTNNY KPSLKDRVTI SRDTSKNQFS LKLSSVTAAD
     TAVYYCARYG
101  RVFFDYWGQG TLVTVSSAST KGPSVFPLAP SSKSTSGGTA
     ALGCLVKDYF
151  PEPVTVSWNS GALTSGVHTF PAVLQSSGLY SLSSVVTVPS
     SSLGTQTYIC
201  NVNHKPSNTK VDKRVEPKSC DKTHTCPPCP APELLGGPSV
     FLFPPKPKDT
```

-continued

```
251  LMISRTPEVT CVVVDVSHED PEVKFNWYVD GVEVHNAKTK
     PREEQYNSTY
301  RVVSVLTVLH QDWLNGKEYK CKVSNKALPA PIEKTISKAK
     GQPREPQVYT
351  LPPSREEMTK NQVSLTCLVK GFYPSDIAVE WESNGQPENN
     YKTTPPVLDS
401  DGSFFLYSKL TVDKSRWQQG NVFSCSVMHE ALHNHYTQKS
     LSLSPGK;
```

or a variable domain thereof or a light chain and/or heavy chain immunoglobulin comprising one or more CDRs (e.g., 3) of the light and/or heavy chain, e.g., those which are underscored in the sequences above.

In an embodiment of the invention, the pAVEC vector comprises polynucleotides encoding the light and/or heavy immunoglobulin chains of antibodies such as Abciximab, Adalimumab, Alemtuzumab, Basiliximab, Bevacizumab, Cetuximab, Certolizumab pegol, Dalotuzumab, Daclizumab, Denosumab, Eculizumab, Efalizumab, Gemtuzumab, Ibritumomab tiuxetan, Infliximab, Muromonab-CD3, Natalizumab, Omalizumab, Palivizumab, Panitumumab, Ranibizumab, Rituximab, Robatumumab, Tositumomab, ALD518 or Trastuzumab. The sequences of such antibodies are known in the art. In an embodiment of the invention, the pAVEC vector comprises a heavy and/or light chain immunoglobulin of an antibody or antigen-binding fragment thereof that binds specifically to an antigen (e.g., from any mammal such as a human or canine or monkey or rat or rabbit or mouse); e.g., an antigen such as VEGF, VEGFR, EGF, EGFR, PD-1, TNFalpha, TGFbeta, TRAIL-R1, TSLP, Nav1.7, Nav1.8, ERK, MEK, TRAIL-R2, IL-10, IL-6, IL-6R, IGF1R, IL-23p19, IL23R, PCSK9, CD20, RANKL, RANK, CD33, CD11a, ErbB2, IgE, a G-protein coupled receptor (GPCR) an HIV antigen, an HCV antigen or a respiratory syncytial virus (RSV) antigen; or an antigen-binding fragment thereof, or a variable domain of any of such antibodies or antigen-binding fragments or a light chain and/or heavy chain immunoglobulin comprising one or more CDRs (e.g., 3) of the light and/or heavy chain of any of such antibodies or antigen-binding fragments. In an embodiment of the invention, the species from which the antigen is derived is the same or different from that of the light and/or heavy chain constant domain; and/or immunoglobulin frameworks.

In an embodiment of the invention, the pAVEC vector comprises a light and/or heavy chain immunoglobulin comprising a member selected from the group consisting of:

(a) an immunoglobulin heavy chain comprising the amino acid sequence:

(SEQ ID NO: 13)

```
E V Q L Q Q S G A E L V K P G A S V T L S C T A S G F N I K D T Y
M H W V N Q R P E Q G L V W I G R I D P A N G H T E Y D P K F Q D
K A T I T T D T S S N T A Y L H L S S L T S G D T A V Y Y C A R S
Y F G S I F A Y W G Q G T L V T V S A;
```

-continued (b) an immunoglobulin light chain comprising the amino acid sequence:
(SEQ ID NO: 14)
Q I V L T Q S P A I M S A S P G E K V T I S C S A S S S V S Y L Y
W Y Q Q K P G S S P K P W I F R S S H R A S G V P A R F S G S G S
G T S Y S L T I S S M E A E D A A T Y Y C H Q Y Q S Y P P T F G G
G T K L E I K R A;

(c) an immunoglobulin heavy chain comprising the amino acid sequence:
(SEQ ID NO: 15)
E V Q L Q Q S G A D L V K P G A S V K L S C T A S G F N I K D T Y
I H W V K Q R P E Q G L E W I G R I D P A N G H T E Y D P K F Q G
R A T L T T D T S S N T A Y L Q L F S L T S E D S A V Y F C A R S
Y Y G S I F A Y W G Q G T L V T V S A;

(d) an immunoglobulin light chain comprising the amino acid sequence:
(SEQ ID NO: 16)
Q I V L T Q S P A I M S A S P G E K V T I S C S A S S S V S Y L F
W Y Q Q K P G S S P K P W I F R T S Y L A S G V P A R F S G S G S
G T S F S L T I S S M E A E D A A T Y Y C H Q Y H T Y P P T F G G
G T K L E I K R A;

(e) an immunoglobulin heavy chain comprising the amino acid sequence:
(SEQ ID NO: 17)
E V Q L Q Q S G A E L V R S G A S V K L S C T T S G F N I K D Y Y
I H W V K Q R P E Q G L E W I G W I D P E N G D T E Y A P K F Q G
K A T M T A D T S S N T A Y L Q L S S L T S A D T A V Y Y C N A
Y Y R Y D D G T W F P Y W G Q G T L V T V S A;

(f) an immunoglobulin light chain comprising the amino acid sequence:
(SEQ ID NO: 18)
D I Q L T Q S P A S L S A S V G E T V T I T C R A S G N I H S Y L
A W Y Q Q K Q G K S P Q F L V D N A K T L P D G V P S R F S V S G
S G T Q Y S L K I N S L Q P E D F G T Y Y C Q H F W N T P W T F G
G G T K L E I K R A;

(g) an immunoglobulin heavy chain comprising the amino acid sequence:
(SEQ ID NO: 19)
E V L L Q Q S V A E L V R P G A S V R L S C T A S G F N I K D T Y
I H W V R Q R P E Q G L E W F G W I D P A N G Y T K Y A P N F Q G
K A T L T T D T S S N T A Y L H L S S L T S E D S A I Y Y C A R G
Y Y R Y Y S L D Y W G Q G T S V T V S S;

(h) an immunoglobulin light chain comprising the amino acid sequence:
(SEQ ID NO: 20)
D I Q M T Q T T S S L S A S L G D R V T I S C R A S Q D I S N Y L
N W Y Q Q K P D G T V K L L I Y Y S S R L H S G V P S R F S G R G
S G T D Y S L T I S T L E Q E D I A T Y F C Q Q G K T L P L T F G
A G T K L E L K R A;

(i) an immunoglobulin heavy chain comprising the amino acid sequence:
(SEQ ID NO: 21)
E V Q L V D S G G G L V Q P G R S L K L S C A A S G F T F S N H D
M A W V R Q A P T K G L E W V A S I T P S G G T T Y Y R D S V E G
R F T V S R D N V K S S L H L Q M D S L T S E D T A T Y Y C A R Q
N Y Y D G S Y Y Y G L Y Y F D Y W G Q G V M V T V S S;

(j) an immunoglobulin light chain comprising the amino acid sequence:
(SEQ ID NO: 22)
D V L M T Q T P V S L P V S L G G Q V S I S C R S S Q S L V Y S D
G N T Y L H W Y L Q K P G Q S P Q L L I Y R V S N R F S G V P D R
F S G S G S G T D F T L K I S R V E P E D L G L Y Y C L Q S T H F
P P T F G S G T K L E I K R A;

(k) an immunoglobulin heavy chain comprising the amino acid sequence:
(SEQ ID NO: 23)
E V Q L Q Q S G P E L V K P G A S V K I S C K V S G Y T F T D Y Y
M N W V K Q S H G K S L E W I G D I N P N N G G A I Y N Q K F K G
K A T L T V D K S S S I A Y M E L R S L T S E D S A V Y Y C T S G
I I T E I A E D F W G Q G T T L T V S S;
and (l) an immunoglobulin light chain comprising the amino acid sequence:
(SEQ ID NO: 24)
D I V M T Q S Q K F M S T S V G D R V S V T C K A S Q N V G T N V
V W Y Q Q K P G Q S P K A L I H S A S Y R Y S G V P D R F K G S G
S G T D F T L T I T N V Q S E D L A G F F C Q Q Y K T Y P Y T F G
G G T Q L E I K R A;

or an immunoglobulin comprising one or more CDRs (e.g., 3) of the light and/or heavy chains set forth above.

Protein Expression and Purification

A further aspect of the present invention relates to a method for the production of a recombinant protein and/or propagation of a particular polynucleotide using a pAVEC plasmid. For example, in an embodiment of the invention, a method for expressing a protein comprises culturing a host cell (e.g., a CHO cell) comprising a pAVEC plasmid having a polynucleotide that encodes a polypeptide (e.g., that is operably linked to a promoter such as the hCMV promoter of pAVEC) under appropriate conditions to enable growth of the host cell comprising the plasmid and expression of the recombinant protein, e.g., a method that comprises the steps of:

a) introducing a polynucleotide encoding a polypeptide of interest (e.g., an immunoglobulin chain) into a pAVEC plasmid (e.g., SEQ ID NO:1), e.g., that is operably linked to a promoter such as the hCMV promoter of pAVEC;

As was discussed above, introducing the polynucleotide into the pAVEC plasmid may result in loss of some pAVEC polynucleotide sequence, e.g., due to excision of a portion of the multiple cloning site so as to generate restriction enzymatically cleaved sites that are compatible for ligation to the ends of the introduced polynucleotide into the plasmid.

b) transfecting a host cell with a pAVEC plasmid comprising the polynucleotide encoding the protein of interest;

The plasmid may be propagated in the host cells either ectopically as an autonomously replicating element (e.g., wherein the plasmid has a high copy number, e.g., about 2, 3, 4, 5, 10, 20 or 50) or integrated into a host cell chromosome.

c) culturing the cell under appropriate conditions to enable growth of the host cell comprising the plasmid and expression of the recombinant protein; and, optionally d) harvesting the polypeptide produced.

Methods for harvesting (isolating and/or purifying) a given protein from, e.g., a cell, a cell culture or the medium in which cells have been cultured are well known in the art. By way of nonlimiting example, proteins can be isolated and/or purified from biological material by salt or alcohol precipitation (e.g., ammonium sulfate precipitation or ethanol precipitation), affinity chromatography (e.g., used in conjunction with a purification tag); fractionation on immunoaffinity or ion-exchange columns; high pressure liquid chromatography (HPLC); reversed-phase HPLC; chromatography on silica or on a cation-exchange resin such as DEAE; chromatofocusing;); isoelectric focusing; countercurrent distribution; SDS-PAGE; gel filtration (using, e.g., Sephadex G-75); and protein A Sepharose columns to remove contaminants such as IgG. Such purification methods are well known in the art and are disclosed, e.g., in *"Guide to Protein Purification", Methods in Enzymology*, Vol. 182, M. Deutscher, Ed., 1990, Academic Press, New York, N.Y.

Growth of mammalian cells in liquid aqueous culture is well known in the art. Examples of mammalian cell culture growth media which are known in the art include EX-CELL® ACF growth medium, CHO medium (Sigma-Aldrich (St. Louis, Mo.); discussed further below), DMEM, DMEM/F-12, F-10 Nutrient Mixture, RPMI Medium 1640, F-12 Nutrient Mixture, Medium 199, Eagle's MEM, RPMI, 293 media, and Iscove's Media.

Cell growth can be performed in any of several systems. For example, cell growth can be done in a simple flask, e.g., a glass shake flask. Other systems include tank bioreactors, bag bioreactors and disposable bioreactors. A tank bioreactor includes, typically, a metal vessel (e.g., a stainless steel jacketed vessel) in which cells are growth in a liquid medium. Tank bioreactors can be used for a wide range of culture volumes (e.g., 100 l, 150 l, 10000 l, 15000 l). Tank bioreactors often have additional features for controlling cell growth conditions, including means for temperature control, medium agitation, controlling sparge gas concentrations, controlling pH, controlling $O_2$ concentration, removing samples from the medium, reactor weight indication and control, cleaning hardware, sterilizing the hardware, piping or tubing to deliver all services, adding media, control pH, control solutions, and control gases, pumping sterile fluids into the growth vessel and, supervisory control and a data acquisition. Classifications of tank bioreactor include stirred tank reactors wherein mechanical stirrers (e.g., impellers) are used to mix the reactor to distribute heat and materials (such as oxygen and substrates). Bubble column reactors are tall reactors which use air alone to mix the contents. Air lift reactors are similar to bubble column reactors, but differ by the fact that they contain a draft tube. The draft tube is typically an inner tube which improves circulation and oxygen transfer and equalizes shear forces in the reactor. In fluidized bed reactors, cells are "immobilized" on small particles which move with the fluid. The small particles create a large surface area for cells to stick to and enable a high rate of transfer of oxygen and nutrients to the cells. In packed bed reactors cells are immobilized on large particles. These particles do not move with the liquid. Packed bed reactors are simple to construct and operate but can suffer from blockages and from poor oxygen transfer. A disposable bioreactor is a disposable, one-time use bioreactor. Often, disposable bioreactors possess features similar to non-disposable bioreactors (e.g., agitation system, sparge, probes, ports, etc.).

Particularly where a polypeptide is isolated from a cellular or tissue source, it is preferable to include one or more inhibitors of proteolytic enzymes in the assay system, such as phenylmethanesulfonyl fluoride (PMSF), PEFABLOC® SC protease inhibitor, pepstatin, leupeptin, chymostatin and EDTA.

In some embodiments, the protein of interest is with a second polypeptide or polynucleotide moiety, which may be referred to as a "tag" or "marker". A tag may be used, for example, to facilitate purification or detection of the polypeptide after expression. A fused polypeptide may be constructed, for example, by in-frame insertion of a polynucleotide encoding the tag on the 5' or 3' end of the polynucleotide encoding the polypeptide to be expressed. The fused polynucleotide may then be expressed in the expression system of the invention. Such tags include glutathione-S-transferase (GST), hexahistidine (His6) tags, maltose binding protein (MBP) tags, haemagglutinin (HA) tags, cellulose binding protein (CBP) tags and myc tags. Detectable tags such as $^{32}P$, $^{35}S$, $^{3}H$, $^{99m}Tc$, $^{123}I$, $^{111}In$, $^{68}Ga$, $^{18}F$, $^{125}I$, $^{131}I$, $^{113m}In$, $^{76}Br$, $^{67}Ga$, $^{99m}Tc$, $^{123}I$, $^{111}In$ and $^{68}Ga$ may also be used to label the polypeptides and polynucleotides of the invention. Methods for constructing and using such fusions are very conventional and well known in the art.

One skilled in the art appreciates that purification methods suitable for the polypeptide of interest may require modification to account for changes in the character of the polypeptide upon expression in recombinant cell culture.

The present invention also relates to a method for the introducing a polynucleotide into a pAVEC plasmid comprising transforming a host cell with the plasmid, e.g., comprising the steps of:

a) cleaving the pAVEC plasmid at the site into which insertion of the polynucleotide is desired (e.g., using a restriction enzyme, e.g., that generates ends that are compatible for hybridization with and subsequent ligation ends of the polynucleotide to be inserted). The ends of the polynucleotide to be inserted may also be generated by a process including cleavage with a restriction enzyme that generates ends compatible with the ends of the cleaved plasmid.

As was discussed above, introducing the polynucleotide into the pAVEC plasmid may result in loss of some pAVEC polynucleotide sequence, e.g., due to excision of a portion of the multiple cloning site so as to generate restriction enzymatically cleaved sites that are compatible for ligation to the ends of the introduced polynucleotide into the plasmid.

b) ligating ends of the cleaved pAVEC with the ends of the polynucleotide (e.g., using a DNA ligase) to generate a final circular recombined plasmid;

b) the recombined plasmid may then be transformed into a host cell wherein the plasmid and the added polynucleotide is propagated. The plasmid may be propagated in the host cells either ectopically as an autonomously replicating element (e.g., wherein the plasmid has a high copy number, e.g., about 2, 3, 4, 5, 10, 20 or 50) or integrated into a host cell chromosome.

Kits

The pAVEC plasmid vectors of the invention may be provided in a kit. The kits of the invention may include, in addition to the plasmid vector, any reagent which may be employed in the use of the plasmid vector. In one embodiment, the kit includes reagents necessary for transformation of the vectors into bacterial and/or mammalian host cells. For example, the kit may include reagents for a calcium phosphate transformation procedure: calcium chloride, buffer (e.g., 2X HEPES buffered saline), and sterile, distilled water. In another embodiment, the kit includes reagents for a DEAE-Dextran transformation: Chloroquine in PBS, DEAE-dextran in PBS and Phosphate buffered saline. In yet another embodiment, reagents for a liposome transformation are included in the kit: Liposomes extruded from DOTAP/cholesterol extruded liposomes. For example, the kit may include the cationic lipid-based transfection reagent LIPOFECTAMINE™ transfection reagent (Invitrogen Life Technologies; Carlsbad, Calif.).

The kit may include reagents required for bacterial transformation of the vectors of the invention. For example, the kit may include transformation competent bacteria (e.g., DH1, DH5, DH5α, XL1-Blue, SURE, SCS110, OneShot Top 10, or HB101).

The kit may include growth media or reagents required for making growth media. For example, in one embodiment, the kit can include fetal calf serum or DMEM (Dulbecco/Vogt modified Eagle's (Harry Eagle) minimal essential medium) for growth of mammalian cells. In another embodiment, the kit can contain powdered Luria broth media or Luria broth plates containing an appropriate antibiotic (e.g., ampicillin or kanamycin) for growing bacteria.

Components supplied in the kit may be provided in appropriate vials or containers (e.g., plastic or glass vials). The kit can include appropriate label directions for storage, and appropriate instructions for usage.

EXAMPLE

The following example is provided to further describe the present invention and should not be construed as a limitation thereof. The scope of the present invention includes any and all of the methods which are set forth below in the following example.

Example 1

Construction of pAVEC Plasmid

The sequence of the multiple cloning site (MCS):

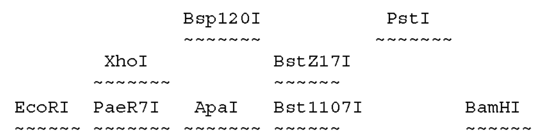

Figure 2:
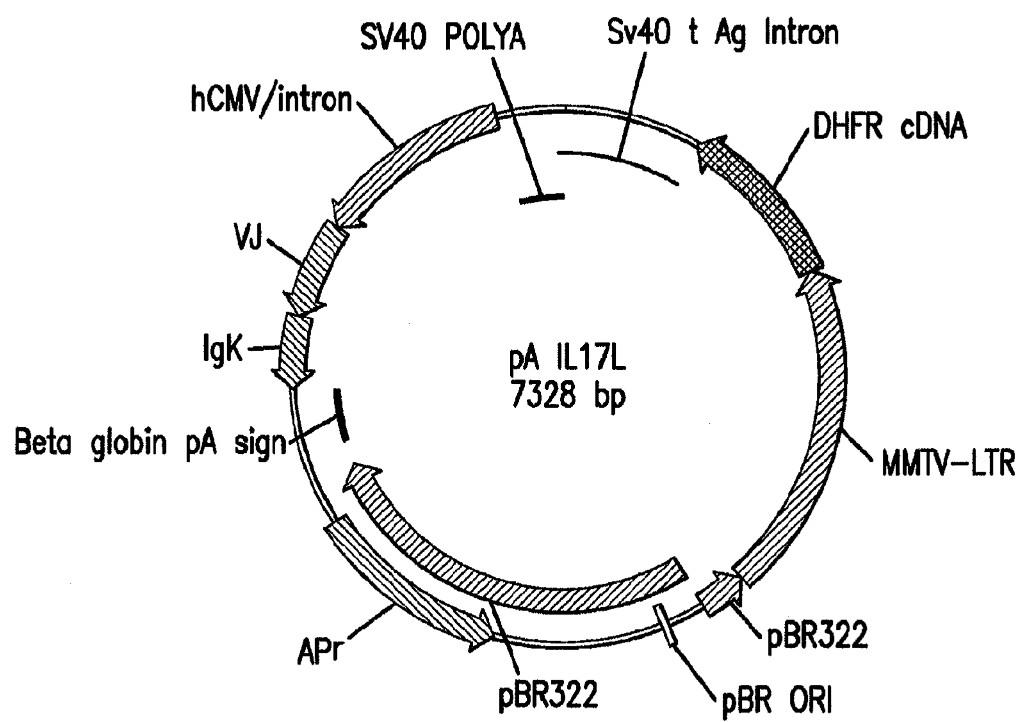
FIG. 2: pAIL17L plasmid map.

(SEQ ID NO: 1)
GAATTCTCTC GAGTGGGCCC AGTATACACT GCAGGGATCC;

was synthesized by polymerase chain reaction (PCR). The PCR product was later digested by the restriction enzymes, EcoRI and BamHI. The vector, pAIL17L (FIG. 2) was also digested by the restriction enzymes EcoRI and BamHI. Finally the digested PCR product was ligated to the digested vector and the transformants were screened for the vector, pAVEC. The multiple cloning site in pAVEC was later analyzed by sequencing for the integrity of the site.

```
Sequence of pAIL17L:
                                                              (SEQ ID NO: 25)
  1 GCACTA TACATC AAATAT TCCTTA TTAACC CCTTTA CAAATT AAAAAG CTAAAG GTACAC

 61 AATTTT TGAGCA TAGTTA TTAATA GCAGAC ACTCTA TGCCTG TGTGGA GTAAGA AAAAAC

121 AGTATG TTATGA TTATAA CTGTTA TGCCTA CTTATA AAGGTT ACAGAA TATTTT TCCATA

181 ATTTTC TTGTAT AGCAGT GCAGCT TTTTCC TTTGTG GTGTAA ATAGCA AAGCAA GCAAGA

241 GTTCTA TTACTA AACACA GCATGA CTCAAA AAACTT AGCAAT TCTGAA GGAAAG TCCTTG

301 GGGTCT TCTACC TTTCTC TTCTTT TTTGGA GGAGTA GAATGT TGAGAG TCAGCA GTAGCC

361 TCATCA TCACTA GATGGC ATTTCT TCTGAG CAAAAC AGGTTT TCCTCA TTAAAG GCATTC

421 CACCAC TGCTCC CATTCA TCAGTT CCATAG GTTGGA ATCTAA AATACA CAAACA ATTAGA

481 ATCAGT AGTTTA ACACAT TATACA CTTAAA AATTTT ATATTT ACCTTA GAGCTT TAAATC

541 TCTGTA GGTAGT TTGTCC AATTAT GTCACA CCACAG AAGTAA GGTTCC TTCACA AAGATC

601 GATCTA AAGCCA GCAAAA GTCCCA TGGTCT TATAAA AATGCA TAGCTT TAGGAG GGGAGC

661 AGAGAA CTTGAA AGCATC TTCCTG TTAGTC TTTCTT CTCGTA GACTTC AAACTT ATACTT
```

-continued

```
 721 GATGCC TTTTTC CTCCTG GACCTC AGAGAG GACGCC TGGGTA TTCTGG GAGAAG TTTATA
 781 TTTCCC CAAATC AATTTC TGGGAA AAACGT GTCACT TTCAAA TTCCTG CATGAT CCTTGT
 841 CACAAA GAGTCT GAGGTG GCCTGG TTGATT CATGGC TTCCTG GTAAAC AGAACT GCCTCC
 901 GACTAT CCAAAC CATGTC TACTTT ACTTGC CAATTC CGGTTG TTCAAT AAGTCT TAAGGC
 961 ATCATC CAAACT TTTGGC AAGAAA ATGAGC TCCTCG TGGTGG TTCTTT GAGTTC TCTACT
1021 GAGAAC TATATT AATTCT GTCCTT TAAAGG TCGATT CTTCTC AGGAAT GGAGAA CCAGGT
1081 TTTCCT ACCCAT AATCAC CAGATT CTGTTT ACCTTC CACTGA AGAGGT TGTGGT CATTCT
1141 TTGGAA GTACTT GAACTC GTTCCT GAGCGG AGGCCA GGGTAG GTCTCC GTTCTT GCCAAT
1201 CCCCAT ATTTTG GGACAC GGCGAC GATGCA GTTCAA TGGTCG AACCAT GATGGC AGCGGG
1261 GATAAA ATCCTA CCAGCC TTCACG CTAGGA TTGCCG TCAAGT TTGGCG CGAAAT CGCAGC
1321 CCTGAG CTGTCC CCCCCC CCAAGC TCAGAT CTGAGC TTGGTC CCTATG GTGAGT CCGTTC
1381 CGCTCT TGTGAT GATAGC CAGACA AGAAAG AGACAA TACAAG ACAAAC ACCAAA TAGTAG
1441 AAATAG AGACAA GGGTCA CTTATC CGAGGG TCCCTG TTCGGG CGCCAG CTGCCG CAGTCG
1501 GCCGAC CTGAGG GTCGCC GGGGTC TGCGGG GGGACC CTCTGG AAAGTG AAGGAT AAGTGA
1561 CGAGCG GAGACG GGATGG CGAACA GACACA AACACA CAAGAG GTGAAT GTTAGG ACTGTT
1621 GCAAGT TTACTC AAAAAA TCAGCA CTCTTT TATATC TTGGTT TACATA AGCATT TACATA
1681 AGATTT GGATAA ATTCCA AAAGAA CATAGG AAAATA GAACAC TCAGAG CTCAGA TCAGAA
1741 CCTTTG ATACCA AACCAA GTCAGG AAACCA CTTGTC TCACAT CCTCGT TTTAAG AACAGT
1801 TTGTAA CCAAAA ACTTAC TTAAGC CCTGGG AACCGC AAGGTT GGGCCA ATAAAG GCTATT
1861 CATAAT AACTCA TGCCAT GAGTTT TTGCAG AATAAT GTTCTA TTAGTC CAGCCA CTGTCC
1921 CCTCCT TGGTAT GGAAAA TCTTTC CCCAAA AGTGCA TTCCTG TTCCTA GATAAA TATAAT
1981 CATGTA CCTGTT GTTTCA TGTCGT CTTTTT CTTCTT GAGACA ACATAC ACCAAG GAGGTC
2041 TAGCTC TGGCGA GTCTTT CACGAA AAGGGA GGGATC TATATA ACACTT TATAGC CATTGA
2101 CTGTAA CCCACC TATCCC AATTTA AGTCAT ATCTTC CTGTAT ATGGTA AGGGGG CATCTG
2161 TTGGTC TGTAGA TGTAAG GTCCCC TATAAG TCCCTG GTTGCC ACCACC TGTCTC CTATTT
2221 TGACAA AAACAC TCTTTT TTCCCT TTTTTA CTTCTA GGCCTG TGGTCA ATAGTC CTTGCA
2281 CCTGTT CTTCAA TTGAGG TTGAGC GTCTCT TTCTAT TTTCTA TTCCCA TTTCTA ACTTCT
2341 GAATTT GAGTAA AAATAG TACTAA AAGATA ATGATT CATTTC TTAACA TAGTAA CTAATA
2401 ATCTAC CTATTG GATTGG TCTTAT TGGTAA AAATAT AATTTT TAGCAA GCATTC TTATTT
2461 CTATTT CTGAAG GACAAA ATCGAT GCGGCT TGTAAG AGGAAG TTGGCT GTGGTC CTTGCC
2521 TCAGGA GGAAGG TCGAGT TCTCCG AATTGT TTAGAT TGTAAT CTTGCA CAGAAG AGCTAT
2581 TAAAAG AGTCAA GGGTGA GAGCCC TGCGAG CACGAA CCGCAA CTTCCC CCAATA GCCCCA
2641 GGCAAA GCAGAG CTATGC CAAGTT TGCAGC AGAGAA TGAATA TGTCTT TGTCTG ATGGGC
2701 TCATCC GTTTGT GCGCAG ACGGGT CGTCCT TGGTGG GAAACA ACCCCT TGGCTG CTTCTC
2761 CCCTAG GTGTAG GACACT CTCGGG AGTTCA ACCATT TCTGCC CAAGCT CAGATC TGAGCT
2821 TTAATG CGGTAG TTTATC ACAGTT AAATTG CTAACG CAGTCA GGCACC GTGTAT GAAATC
2881 TAACAA TGCGCT CATCGT CATCCT CGGCAC CGTCAC CCTGGA TGCTGT AGGCAT AGGCTT
2941 GGTTAT GCCGGT ACTGCC GGGCCT CTTGCG GGATAT CGTCCA TTCCGA CAGCAT CGCCAG
3001 TCACTA TGGCGT GCTGCT AGCGCT CTTCCG CTTCCT CGCTCA CTGACT CGCTGC GCTCGG
3061 TCGTTC GGCTGC GGCGAG CGGTAT CAGCTC ACTCAA AGGCGG TAATAC GGTTAT CCACAG
```

-continued

3121 AATCAG GGGATA ACGCAG GAAAGA ACATGT GAGCAA AAGGCC AGCAAA AGGCCA GGAACC

3181 GTAAAA AGGCCG CGTTGC TGGCGT TTTTCC ATAGGC TCCGCC CCCCTG ACGAGC ATCACA

3241 AAAATC GACGCT CAAGTC AGAGGT GGCGAA ACCCGA CAGGAC TATAAA GATACC AGGCGT

3301 TTCCCC CTGGAA GCTCCC TCGTGC GCTCTC CTGTTC CGACCC TGCCGC TTACCG GATACC

3361 TGTCCG CCTTTC TCCCTT CGGGAA GCGTGG CGCTTT CTCATA GCTCAC GCTGTA GGTATC

3421 TCAGTT CGGTGT AGGTCG TTCGCT CCAAGC TGGGCT GTGTGC ACGAGC CCCCCG TTCAGC

3481 CCGACC GCTGCG CCTTAT CCGGTA ACTATC GTCTTG AGTCCA ACCCGG TAAGAC ACGACT

3541 TATCGC CACTGG CAGCAG CCACTG GTAACA GGATTA GCAGAG CGAGGT ATGTAG GCGGTG

3601 CTACAG AGTTCT TGAAGT GGTGGC CTAACT ACGGCT ACACTA GAAGGA CAGTAT TTGGTA

3661 TCTGCG CTCTGC TGAAGC CAGTTA CCTTCG GAAAAA GAGTTG GTAGCT CTTGAT CCGGCA

3721 AACAAA CCACCG CTGGTA GCGGTG GTTTTT TTGTTT GCAAGC AGCAGA TTACGC GCAGAA

3781 AAAAAG GATCTC AAGAAG ATCCTT TGATCT TTTCTA CGGGGT CTGACG CTCAGT GGAACG

3841 AAAACT CACGTT AAGGGA TTTTGG TCATGA GATTAT CAAAAA GGATCT TCACCT AGATCC

3901 TTTTAA ATTAAA AATGAA GTTTTA AATCAA TCTAAA GTATAT ATGAGT AAACTT GGTCTG

3961 ACAGTT ACCAAT GCTTAA TCAGTG AGGCAC CTATCT CAGCGA TCTGTC TATTTC GTTCAT

4021 CCATAG TTGCCT GACTCC CCGTCG TGTAGA TAACTA CGATAC GGGAGG GCTTAC CATCTG

4081 GCCCCA GTGCTG CAATGA TACCGC GAGACC CACGCT CACCGG CTCCAG ATTTAT CAGCAA

4141 TAAACC AGCCAG CCGGAA GGGCCG AGCGCA GAAGTG GTCCTG CAACTT TATCCG CCTCCA

4201 TCCAGT CTATTA ATTGTT GCCGGG AAGCTA GAGTAA GTAGTT CGCCAG TTAATA GTTTGC

4261 GCAACG TTGTTG CCATTG CTACAG GCATCG TGGTGT CACGCT CGTCGT TTGGTA TGGCTT

4321 CATTCA GCTCCG GTTCCC AACGAT CAAGGC GAGTTA CATGAT CCCCCA TGTTGT GCAAAA

4381 AAGCGG TTAGCT CCTTCG GTCCTC CGATCG TTGTCA GAAGTA AGTTGG CCGCAG TGTTAT

4441 CACTCA TGGTTA TGGCAG CACTGC ATAATT CTCTTA CTGTCA TGCCAT CCGTAA GATGCT

4501 TTTCTG TGACTG GTGAGT ACTCAA CCAAGT CATTCT GAGAAT AGTGTA TGCGGC GACCGA

4561 GTTGCT CTTGCC CGGCGT CAACAC GGGATA ATACCG CGCCAC ATAGCA GAACTT TAAAAG

4621 TGCTCA TCATTG GAAAAC GTTCTT CGGGGC GAAAAC TCTCAA GGATCT TACCGC TGTTGA

4681 GATCCA GTTCGA TGTAAC CCACTC GTGCAC CCAACT GATCTT CAGCAT CTTTTA CTTTCA

4741 CCAGCG TTTCTG GGTGAG CAAAAA CAGGAA GGCAAA ATGCCG CAAAAA AGGGAA TAAGGG

4801 CGACAC GGAAAT GTTGAA TACTCA TACTCT TCCTTT TTCAAT ATTATT GAAGCA TTTATC

4861 AGGGTT ATTGTC TCATGA GCGGAT ACATAT TTGAAT GTATTT AGAAAA ATAAAC AAATAG

4921 GGGTTC CGCGCA CATTTC CCCGAA AAGTGC CACCTG ACGTCT AAGAGA CCATTA TTATCA

4981 TGACAT TAACCT ATAAAA ATAGGC GTATCA CGAGGC CCTTTC GTCTTC AAGAAT TGTCTA

5041 GAGGCG CGCCGT TTAAAC CCTCAG CTGATC ATCCGG ATGTAC AGCGCG CGGCCG GCCGGT

5101 ACCACG CGTTGG CCACAT ATGGCG GCCGCT CGCGAT TAATTA ATCGCG ATGGCC ACATAT

5161 GGAGCT CTCTAG AGCTTG TCGACA GATCCC CCTCTT CATTTC TTTATG TTTTAA ATGCAC

5221 TGACCT CCCACA TTCCCT TTTTAG TAAAAT ATTCAG AAATAA TTTAAA TACATC ATTGCA

5281 ATGAAA ATAAAT GTTTTT TATTAG GCAGAA TCCAGA TGCTCA AGGCCC TTCATA ATATCC

5341 CCCAGT TTAGTA GTTGGA CTTAGG GAACAA AGGAAC CTTTAA TAGAAA TTGGAC AGCAAG

BamHI

5401 AAAGCG AGGGGG ATCTGG ATCCTC CGGAGG GCCCCT TCTCCC TCTAAC ACTCTC CCCTGT

5461 TGAAGC TCTTTG TGACGG GCGAGC TCAGGC CCTGAT GGGTGA CTTCGC AGGCGT AGACTT

5521 TGTGTT TCTCGT AGTCTG CTTTGC TCAGCG TCAGGG TGCTGC TGAGGC TGTAGG TGCTGT

-continued

```
5581 CCTTGC TGTCCT GCTCTG TGACAC TCTCCT GGGAGT TACCCG ATTGGA GGGCGT TATCCA

5641 CCTTCC ACTGTA CTTTGG CCTCTC TGGGAT AGAAGT TATTCA GCAGGC ACACAA CAGAGG

5701 CAGTTC CAGATT TCAACT GCTCAT CAGATG GCGGGA AGATGA AGACAG ATGGTG CAGCCA

5761 CCGTAC GTTTGA TTTCCA CCTTGG TCCCCT GTCCAA AGGTGT AGGGTG TGTAAT AGCTCT

5821 GCTGAC AGTAGT ACACGC CCACAT CTTCGG CCTCCA CCCGGC TGATCT TCAGAG TGAAAT

5881 CTGTCC CAGATC CGCTGC CGCTGA ACCTGT CTGGCA CCCCGC TCTGCC GGGTGC TGGTCC

5941 AATAGA TCAGCA GCTGAG GGCTCT GCCCTG GTTTCT GCAGAT ACCAGG CCAGGT AGTTCT

6001 TCTGGT TCTCGC TGAACA GCAGGC TCTGGC TGCTCT TGCAGC TGATGC TGGCTG GCTCTC

6061 CGGGTG TCACAG GCAGGG ACAGTG GAGACT GGGTCA TCACGA TATCAC ATCTCA TGGCTG
                                                                EcoRI
6121 GCAGGA ACAGCA CCAGCA GCCCCA GCAGCT GCACTG GAGCCA TGGTGG CGGCGC TAGCGA

 EcoRI
6181 ATTCTT AAGCCT GTGGAG AGAAAG GAACAG AAAACG AAACAA AGACGT AGAGTT GAGCAA

6241 GCAGGG TCAGGC AAAGCG TGGAGA GCCGGC TGAGTC TAGGTA GGCTCC AAGGGA GCGCCG

6301 GACAAA GGCCCG GTCTCG ACCTGA GCTTTA AACTTA CCTGTG GCCACA CGTGCA ATTGCT

6361 ATAGTG AGTCGT ATTAAT TTCGAT AAGCCA GTAAGC AGTGGG TTCTCT AGTTAG CCAGAG

6421 AGCTCT GCTTAT ATAGAC CTCCCA CCGTAC ACGCCT ACCGCC CATTTG CGTCAA TGGGGC

6481 GGAGTT GTTACG ACATTT TGGAAA GTCCCG TTGATT TTGGTG CCAAAA CAAACT CCCATT

6541 GACGTC AATGGG GTGGAG ACTTGG AAATCC CCGTGA GTCAAA CCGCTA TCCACG CCCATT

6601 GATGTA CTGCCA AAACCG CATCAC CATGGT AATAGC GATGAC TAATAC GTAGAT GTACTG

6661 CCAAGT AGGAAA GTCCCA TAAGGT CATGTA CTGGGC ATAATG CCAGGC GGGCCA TTTACC

6721 GTCATT GACGTC AATAGG GGGCGT ACTTGG CATATG ATACAC TTGATG TACTGC CAAGTG

6781 GGCAGT TTACCG TAAATA GTCCAC CCATTG ACGTCA ATGGAA AGTCCC TATTGG CGTTAC

6841 TATGGG AACATA CGTCAT TATTGA CGTCAA TGGGCG GGGGTC GTTGGG CGGTCA GCCAGG

6901 CGGGCC ATTTAC CGTAAG TTATGT AACGCG GAACTC CATATA TGGGCT ATGAAC TAATGA

6961 CCCCGT AATTGA TTACTA TTAATA ACTAGT CAATAA TCAATG TCAACG CGTATA TCTGGC

7021 CCGTAC ATCGGT AACTAG TCGGAC CGGCCC GGGCCA CCGGTG CTCGAA GCTTGG ATCGAT

7081 CCAGAC ATGATA AGATAC ATTGAT GAGTTT GGACAA ACCACA ACTAGA ATGCAG TGAAAA

7141 AAATGC TTTATT TGTGAA ATTTGT GATGCT ATTGCT TTATTT GTAACC ATTATA AGCTGC

7201 AATAAA CAAGTT AACAAC AACAAT TGCATT CATTTT ATGTTT CAGGTT CAGGGG GAGGTG

7261 TGGGAG GTTTTT TAAAGC AAGTAA AACCTC TACAAA TGTGGT ATGGCT GATTAT GATCTC

7321 TAGTCA AG
```

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

Patents, patent applications, publications, product descriptions, and protocols are cited throughout this application, the disclosures of which are incorporated herein by reference in their entireties for all purposes.

I claim:

1. An isolated vector having the plasmid map of FIG. 1 which comprises a multiple cloning site that comprises the nucleotide sequence set forth in SEQ ID NO: 1.

2. The vector of claim 1, comprising the polynucleotide sequence set forth in SEQ ID NO: 2.

3. A method for making a recombined plasmid vector comprising cleaving the vector of claim 1 and ligating the ends of the cleaved plasmid to compatible ends of an introduced polynucleotide such that a closed circular plasmid is produced.

4. The method of claim 3 wherein the introduced polynucleotide encodes an immunoglobulin chain.

5. The method of claim 4 wherein the immunoglobulin chain is a heavy or light chain of a member selected from the group consisting of: Abciximab, Adalimumab, Alemtuzumab, Basiliximab, Bevacizumab, Cetuximab, Certolizumab, Pegol, Dalotuzumab, Daclizumab, Denosumab, Eculizumab, Efalizumab, Gemtuzumab, Ibritumomab, Tiuxetan, Infliximab, Muromonab-CD3, Natalizumab, Omalizumab, Palivizumab, Panitumumab, Ranibizumab, Rituximab, Robatumumab, Tositumomab, ALD518 and Trastuzumab;

or, wherein the immunoglobulin chain is a heavy or light chain of an antibody or antigen-binding fragment thereof that binds specifically to an antigen selected from the group consisting of: vascular endothelial growth factor (VEGF), vascular endothelial grown factor receptor (VEGFR), epidermal growth factor (EGF), epidermal growth factor receptor (EGFR), programmed cell death protein 1 (PD-1), tumor necrosis factor alpha (TNFalpha), tumor necrosis factor beta (TGFbeta), TRAIL-R1, thymic stromal lymphopoietin (TSLP), Nav1.7, Nav1.8, extracellular signal-related kinase (ERK), MEK, TRAIL-R2, interleukin-10 (IL-10), interleukin-6 (IL-6), interleukin-6 receptor (IL-6R), insulin-like growth factor-1 receptor (IGF1R), interleukin-23p19 (IL-23p19), interleukin-23 receptor (IL-23R), proprotein convertase subtilisin/kexin type 9 (PCSK9), CD20, receptor activator of nuclear factor kappa-B ligand (RANKL), receptor activator of nuclear factor kappa-B (RANK), CD33, CD11a, ErbB2, IgE, a G-protein coupled receptor (GPCR), a human immunodeficiency virus (HIV) antigen, a hepatitis C virus (HCV) antigen, and a respiratory syncytial virus (RSV) antigen.

6. A recombined plasmid vector that is the product of the method according to claim 3.

7. An isolated host cell comprising the vector of claim 1.

8. The host cell of claim 7 which is a bacterial or mammalian cell.

9. A method for producing a recombinant polypeptide in an isolated host cell, comprising introducing the recombined vector of claim 6 into a host cell; and expressing the polypeptide from the introduced polynucleotide.

10. The method of claim 9, further comprising purifying the polypeptide.

11. A kit comprising a plasmid vector of claim 1 and one or more additional components.

* * * * *

SEQUENCE LISTING

```
<160> NUMBER OF SEQ ID NOS: 25

<210> SEQ ID NO 1
<211> LENGTH: 40
<212> TYPE: DNA
<213> ORGANISM: Artificial Sequence
<220> FEATURE:
<223> OTHER INFORMATION: pAVEC multiple cloning site

<400> SEQUENCE: 1

gaattctctc gagtgggccc agtatacact gcagggatcc                              40


<210> SEQ ID NO 2
<211> LENGTH: 6599
<212> TYPE: DNA
<213> ORGANISM: Artificial Sequence
<220> FEATURE:
<223> OTHER INFORMATION: pAVEC plasmid sequence

<400> SEQUENCE: 2

cttgactaga gatcataatc agccatacca catttgtaga ggttttactt gctttaaaaa      60

acctcccaca cctccccctg aacctgaaac ataaaatgaa tgcaattgtt gttgttaact     120

tgtttattgc agcttataat ggttacaaat aaagcaatag catcacaaat ttcacaaata     180

aagcattttt ttcactgcat tctagttgtg gtttgtccaa actcatcaat gtatcttatc     240

atgtctggat cgatccaagc ttcgagcacc ggtggcccgg gccggtccga ctagttacga     300

tgtacgggcc agatatacgc gttgacattg attattgact agttattaat agtaatcaat     360

tacggggtca ttagttcata gcccatatat ggagttccgc gttacataac ttacggtaaa     420

tggcccgcct ggctgaccgc ccaacgaccc ccgcccattg acgtcaataa tgacgtatgt     480

tcccatagta acgccaatag ggactttcca ttgacgtcaa tgggtggagt atttacggta     540

aactgcccac ttggcagtac atcaagtgta tcatatgcca agtacgcccc ctattgacgt     600

caatgacggt aaatggcccg cctggcatta tgcccagtac atgaccttat gggactttcc     660

tacttggcag tacatctacg tattagtcat cgctattacc atggtgatgc ggttttggca     720

gtacatcaat gggcgtggat agcggtttga ctcacgggga tttccaagtc tccaccccat     780

tgacgtcaat gggagtttgt tttggcacca aaatcaacgg gactttccaa aatgtcgtaa     840

caactccgcc ccattgacgc aaatgggcgg taggcgtgta cggtgggagg tctatataag     900

cagagctctc tggctaacta gagaacccac tgcttactgg cttatcgaaa ttaatacgac     960

tcactatagc aattgcacgt gtggccacag gtaagtttaa agctcaggtc gagaccgggc    1020

ctttgtccgg cgctcccttg gagcctacct agactcagcc ggctctccac gctttgcctg    1080

accctgcttg ctcaactcta cgtctttgtt tcgttttctg ttcctttctc tccacaggct    1140

taagaattct ctcgagtggg cccagtatac actgcaggga tccagatccc cctcgctttc    1200

ttgctgtcca atttctatta aaggttcctt tgttccctaa gtccaactac taaactgggg    1260

gatattatga agggccttga gcatctggat tctgcctaat aaaaaacatt tattttcatt    1320

gcaatgatgt atttaaatta tttctgaata ttttactaaa aagggaatgt gggaggtcag    1380
```

-continued

```
tgcatttaaa acataaagaa atgaagaggg ggatctgtcg acaagctcta gagagctcca   1440
tatgtggcca tcgcgattaa ttaatcgcga gcggccgcca tatgtggcca acgcgtggta   1500
ccggccggcc gcgcgctgta catccggatg atcagctgag ggtttaaacg gcgcgcctct   1560
agacaattct tgaagacgaa agggcctcgt gatacgccta tttttatagg ttaatgtcat   1620
gataataatg gtttcttaga cgtcaggtgg cacttttcgg ggaaatgtgc gcggaacccc   1680
tatttgttta tttttctaaa tacattcaaa tatgtatccg ctcatgagac aataaccctg   1740
ataaatgctt caataatatt gaaaaaggaa gagtatgagt attcaacatt tccgtgtcgc   1800
ccttattccc ttttttgcgg cattttgcct tcctgttttt gctcacccag aaacgctggt   1860
gaaagtaaaa gatgctgaag atcagttggg tgcacgagtg ggttacatcg aactggatct   1920
caacagcggt aagatccttg agagttttcg ccccgaagaa cgttttccaa tgatgagcac   1980
ttttaaagtt ctgctatgtg gcgcggtatt atcccgtgtt gacgccgggc aagagcaact   2040
cggtcgccgc atacactatt ctcagaatga cttggttgag tactcaccag tcacagaaaa   2100
gcatcttacg gatggcatga cagtaagaga attatgcagt gctgccataa ccatgagtga   2160
taacactgcg gccaacttac ttctgacaac gatcggagga ccgaaggagc taaccgcttt   2220
tttgcacaac atgggggatc atgtaactcg ccttgatcgt tgggaaccgg agctgaatga   2280
agccatacca aacgacgagc gtgacaccac gatgcctgta gcaatggcaa caacgttgcg   2340
caaactatta actggcgaac tacttactct agcttcccgg caacaattaa tagactggat   2400
ggaggcggat aaagttgcag gaccacttct gcgctcggcc cttccggctg gctggtttat   2460
tgctgataaa tctggagccg gtgagcgtgg gtctcgcggt atcattgcag cactggggcc   2520
agatggtaag ccctcccgta tcgtagttat ctacacgacg gggagtcagg caactatgga   2580
tgaacgaaat agacagatcg ctgagatagg tgcctcactg attaagcatt ggtaactgtc   2640
agaccaagtt tactcatata tactttagat tgatttaaaa cttcattttt aatttaaaag   2700
gatctaggtg aagatccttt ttgataatct catgaccaaa atcccttaac gtgagttttc   2760
gttccactga gcgtcagacc ccgtagaaaa gatcaaagga tcttcttgag atcctttttt   2820
tctgcgcgta atctgctgct tgcaaacaaa aaaaccaccg ctaccagcgg tggtttgttt   2880
gccggatcaa gagctaccaa ctctttttcc gaaggtaact ggcttcagca gagcgcagat   2940
accaaatact gtccttctag tgtagccgta gttaggccac cacttcaaga actctgtagc   3000
accgcctaca tacctcgctc tgctaatcct gttaccagtg gctgctgcca gtggcgataa   3060
gtcgtgtctt accgggttgg actcaagacg atagttaccg gataaggcgc agcggtcggg   3120
ctgaacgggg ggttcgtgca cacagcccag cttggagcga acgacctaca ccgaactgag   3180
atacctacag cgtgagctat gagaaagcgc cacgcttccc gaagggagaa aggcggacag   3240
gtatccggta agcggcaggg tcggaacagg agagcgcacg agggagcttc caggggggaaa   3300
cgcctggtat ctttatagtc ctgtcgggtt tcgccacctc tgacttgagc gtcgattttt   3360
gtgatgctcg tcaggggggc ggagcctatg gaaaaacgcc agcaacgcgg cctttttacg   3420
gttcctggcc ttttgctggc cttttgctca catgttcttt cctgcgttat cccctgattc   3480
tgtggataac cgtattaccg cctttgagtg agctgatacc gctcgccgca gccgaacgac   3540
cgagcgcagc gagtcagtga gcgaggaagc ggaagagcgc tagcagcacg ccatagtgac   3600
tggcgatgct gtcggaatgg acgatatccc gcaagaggcc cggcagtacc ggcataacca   3660
agcctatgcc tacagcatcc agggtgacgg tgccgaggat gacgatgagc gcattgttag   3720
```

```
atttcataca cggtgcctga ctgcgttagc aatttaactg tgataaacta ccgcattaaa   3780
gctcagatct gagcttgggc agaaatggtt gaactcccga gagtgtccta cacctagggg   3840
agaagcagcc aaggggttgt ttcccaccaa ggacgacccg tctgcgcaca aacggatgag   3900
cccatcagac aaagacatat tcattctctg ctgcaaactt ggcatagctc tgctttgcct   3960
ggggctattg ggggaagttg cggttcgtgc tcgcagggct ctcacccttg actcttttaa   4020
tagctcttct gtgcaagatt acaatctaaa caattcggag aactcgacct tcctcctgag   4080
gcaaggacca cagccaactt cctcttacaa gccgcatcga ttttgtcctt cagaaataga   4140
aataagaatg cttgctaaaa attatatttt taccaataag accaatccaa taggtagatt   4200
attagttact atgttaagaa atgaatcatt atcttttagt actattttta ctcaaattca   4260
gaagttagaa atgggaatag aaaatagaaa gagacgctca acctcaattg aagaacaggt   4320
gcaaggacta ttgaccacag gcctagaagt aaaaaaggga aaaaagagtg tttttgtcaa   4380
aataggagac aggtggtggc aaccagggac ttatagggga ccttacatct acagaccaac   4440
agatgccccc ttaccatata caggaagata tgacttaaat tgggataggt gggttacagt   4500
caatggctat aaagtgttat atagatccct ccccttttcgt gaaagactcg ccagagctag   4560
acctccttgg tgtatgttgt ctcaagaaga aaaagacgac atgaaacaac aggtacatga   4620
ttatatttat ctaggaacag gaatgcactt ttggggaaag attttccata ccaaggaggg   4680
gacagtggct ggactaatag aacattattc tgcaaaaact catggcatga gttattatga   4740
atagccttta ttggcccaac cttgcggttc ccagggctta agtaagtttt tggttacaaa   4800
ctgttcttaa aacgaggatg tgagacaagt ggtttcctga cttggtttgg tatcaaaggt   4860
tctgatctga gctctgagtg ttctattttc ctatgttctt ttggaattta tccaaatctt   4920
atgtaaatgc ttatgtaaac caagatataa aagagtgctg atttttttgag taaacttgca   4980
acagtcctaa cattcacctc ttgtgtgttt gtgtctgttc gccatcccgt ctccgctcgt   5040
cacttatcct tcactttcca gagggtcccc ccgcagaccc cggcgaccct caggtcggcc   5100
gactgcggca gctggcgccc gaacagggac cctcggataa gtgacccttg tctctatttc   5160
tactatttgg tgtttgtctt gtattgtctc tttcttgtct ggctatcatc acaagagcgg   5220
aacggactca ccatagggac caagctcaga tctgagcttg gggggggga cagctcaggg   5280
ctgcgatttc gcgccaaact tgacggcaat cctagcgtga aggctggtag gattttatcc   5340
ccgctgccat catggttcga ccattgaact gcatcgtcgc cgtgtcccaa aatatgggga   5400
ttggcaagaa cggagaccta ccctggcctc cgctcaggaa cgagttcaag tacttccaaa   5460
gaatgaccac aacctcttca gtggaaggta aacagaatct ggtgattatg ggtaggaaaa   5520
cctggttctc cattcctgag aagaatcgac ctttaaagga cagaattaat atagttctca   5580
gtagagaact caaagaacca ccacgaggag ctcattttct tgccaaaagt ttggatgatg   5640
ccttaagact tattgaacaa ccggaattgg caagtaaagt agacatggtt tggatagtcg   5700
gaggcagttc tgtttaccag gaagccatga atcaaccagg ccacctcaga ctctttgtga   5760
caaggatcat gcaggaattt gaaagtgaca cgtttttccc agaaattgat ttggggaaat   5820
ataaacttct cccagaatac ccaggcgtcc tctctgaggt ccaggaggaa aaaggcatca   5880
agtataagtt tgaagtctac gagaagaaag actaacagga agatgctttc aagttctctg   5940
ctcccctcct aaagctatgc atttttataa gaccatggga cttttgctgg ctttagatcg   6000
atctttgtga aggaacctta cttctgtggt gtgacataat tggacaaact acctacagag   6060
atttaaagct ctaaggtaaa tataaaattt ttaagtgtat aatgtgttaa actactgatt   6120
```

```
ctaattgttt gtgtatttta gattccaacc tatggaactg atgaatggga gcagtggtgg   6180

aatgccttta atgaggaaaa cctgttttgc tcagaagaaa tgccatctag tgatgatgag   6240

gctactgctg actctcaaca ttctactcct ccaaaaaaga agagaaaggt agaagacccc   6300

aaggactttc cttcagaatt gctaagtttt ttgagtcatg ctgtgtttag taatagaact   6360

cttgcttgct ttgctattta caccacaaag gaaaaagctg cactgctata caagaaaatt   6420

atggaaaaat attctgtaac ctttataagt aggcataaca gttataatca taacatactg   6480

ttttttctta ctccacacag gcatagagtg tctgctatta ataactatgc tcaaaaattg   6540

tgtaccttta gctttttaat ttgtaaaggg gttaataagg aatatttgat gtatagtgc    6599


<210> SEQ ID NO 3
<211> LENGTH: 128
<212> TYPE: PRT
<213> ORGANISM: Homo sapiens

<400> SEQUENCE: 3

Met Ser Pro Ser Gln Leu Ile Gly Phe Leu Leu Leu Trp Val Pro Ala
1               5                   10                  15

Ser Arg Gly Glu Ile Val Leu Thr Gln Val Pro Asp Phe Gln Ser Val
            20                  25                  30

Thr Pro Lys Glu Lys Val Thr Ile Thr Cys Arg Ala Ser Gln Ser Ile
        35                  40                  45

Gly Ser Ser Leu His Trp Tyr Gln Gln Lys Pro Asp Gln Ser Pro Lys
    50                  55                  60

Leu Leu Ile Lys Tyr Ala Ser Gln Ser Leu Ser Gly Val Pro Ser Arg
65                  70                  75                  80

Phe Ser Gly Ser Gly Ser Gly Thr Asp Phe Thr Leu Thr Ile Asn Ser
                85                  90                  95

Leu Glu Ala Glu Asp Ala Ala Ala Tyr Tyr Cys His Gln Ser Ser Arg
            100                 105                 110

Leu Pro His Thr Phe Gly Gly Gly Thr Lys Val Glu Ile Lys Arg Thr
        115                 120                 125


<210> SEQ ID NO 4
<211> LENGTH: 137
<212> TYPE: PRT
<213> ORGANISM: Homo sapiens

<400> SEQUENCE: 4

Met Glu Phe Gly Leu Ser Trp Val Phe Leu Val Ala Ile Leu Lys Gly
1               5                   10                  15

Val Gln Cys Glu Val Gln Leu Val Gln Ser Gly Gly Gly Leu Val His
            20                  25                  30

Pro Gly Gly Ser Leu Arg Leu Ser Cys Ala Ala Ser Gly Phe Thr Phe
        35                  40                  45

Ser Ser Phe Ala Met His Trp Val Arg Gln Ala Pro Gly Lys Gly Leu
    50                  55                  60

Glu Trp Ile Ser Val Ile Asp Thr Arg Gly Ala Thr Tyr Tyr Ala Asp
65                  70                  75                  80

Ser Val Lys Gly Arg Phe Thr Ile Ser Arg Asp Asn Ala Lys Asn Ser
                85                  90                  95

Leu Tyr Leu Gln Met Asn Ser Leu Arg Ala Glu Asp Met Ala Val Tyr
            100                 105                 110

Tyr Cys Ala Arg Leu Gly Asn Phe Tyr Tyr Gly Met Asp Val Trp Gly
```

```
        115                 120                 125

Gln Gly Thr Thr Val Thr Val Ser Ser
    130                 135
```

<210> SEQ ID NO 5
<211> LENGTH: 128
<212> TYPE: PRT
<213> ORGANISM: Homo sapiens

<400> SEQUENCE: 5

```
Met Ser Pro Ser Gln Leu Ile Gly Phe Leu Leu Leu Trp Val Pro Ala
1               5                   10                  15

Ser Arg Gly Glu Ile Val Leu Thr Gln Ser Pro Asp Ser Leu Ser Val
            20                  25                  30

Thr Pro Gly Glu Arg Val Thr Ile Thr Cys Arg Ala Ser Gln Ser Ile
        35                  40                  45

Gly Ser Ser Leu His Trp Tyr Gln Gln Lys Pro Gly Gln Ser Pro Lys
    50                  55                  60

Leu Leu Ile Lys Tyr Ala Ser Gln Ser Leu Ser Gly Val Pro Ser Arg
65                  70                  75                  80

Phe Ser Gly Ser Gly Ser Gly Thr Asp Phe Thr Leu Thr Ile Ser Ser
                85                  90                  95

Leu Glu Ala Glu Asp Ala Ala Ala Tyr Tyr Cys His Gln Ser Ser Arg
            100                 105                 110

Leu Pro His Thr Phe Gly Gln Gly Thr Lys Val Glu Ile Lys Arg Thr
        115                 120                 125
```

<210> SEQ ID NO 6
<211> LENGTH: 128
<212> TYPE: PRT
<213> ORGANISM: Homo sapiens

<400> SEQUENCE: 6

```
Met Ser Pro Ser Gln Leu Ile Gly Phe Leu Leu Leu Trp Val Pro Ala
1               5                   10                  15

Ser Arg Gly Glu Ile Val Leu Thr Gln Ser Pro Asp Ser Leu Ser Val
            20                  25                  30

Thr Pro Gly Glu Arg Val Thr Ile Thr Cys Arg Ala Ser Gln Ser Ile
        35                  40                  45

Gly Ser Ser Leu His Trp Tyr Gln Gln Lys Pro Gly Gln Ser Pro Lys
    50                  55                  60

Leu Leu Ile Lys Tyr Ala Ser Gln Ser Leu Ser Gly Val Pro Ser Arg
65                  70                  75                  80

Phe Ser Gly Ser Gly Ser Gly Thr Asp Phe Thr Leu Thr Ile Ser Ser
                85                  90                  95

Leu Glu Ala Glu Asp Phe Ala Val Tyr Tyr Cys His Gln Ser Ser Arg
            100                 105                 110

Leu Pro His Thr Phe Gly Gln Gly Thr Lys Val Glu Ile Lys Arg Thr
        115                 120                 125
```

<210> SEQ ID NO 7
<211> LENGTH: 128
<212> TYPE: PRT
<213> ORGANISM: Homo sapiens

<400> SEQUENCE: 7

```
Met Ser Pro Ser Gln Leu Ile Gly Phe Leu Leu Leu Trp Val Pro Ala
1               5                   10                  15
```

```
Ser Arg Gly Glu Ile Val Leu Thr Gln Ser Pro Gly Thr Leu Ser Val
            20                  25                  30

Ser Pro Gly Glu Arg Ala Thr Leu Ser Cys Arg Ala Ser Gln Ser Ile
        35                  40                  45

Gly Ser Ser Leu His Trp Tyr Gln Gln Lys Pro Gly Gln Ala Pro Arg
    50                  55                  60

Leu Leu Ile Lys Tyr Ala Ser Gln Ser Leu Ser Gly Ile Pro Asp Arg
65                  70                  75                  80

Phe Ser Gly Ser Gly Ser Gly Thr Asp Phe Thr Leu Thr Ile Ser Arg
                85                  90                  95

Leu Glu Pro Glu Asp Ala Ala Ala Tyr Tyr Cys His Gln Ser Ser Arg
            100                 105                 110

Leu Pro His Thr Phe Gly Gln Gly Thr Lys Val Glu Ile Lys Arg Thr
        115                 120                 125


<210> SEQ ID NO 8
<211> LENGTH: 128
<212> TYPE: PRT
<213> ORGANISM: Homo sapiens

<400> SEQUENCE: 8

Met Ser Pro Ser Gln Leu Ile Gly Phe Leu Leu Leu Trp Val Pro Ala
1               5                   10                  15

Ser Arg Gly Glu Ile Val Leu Thr Gln Ser Pro Gly Thr Leu Ser Val
            20                  25                  30

Ser Pro Gly Glu Arg Ala Thr Leu Ser Cys Arg Ala Ser Gln Ser Ile
        35                  40                  45

Gly Ser Ser Leu His Trp Tyr Gln Gln Lys Pro Gly Gln Ala Pro Arg
    50                  55                  60

Leu Leu Ile Lys Tyr Ala Ser Gln Ser Leu Ser Gly Ile Pro Asp Arg
65                  70                  75                  80

Phe Ser Gly Ser Gly Ser Gly Thr Asp Phe Thr Leu Thr Ile Ser Arg
                85                  90                  95

Leu Glu Pro Glu Asp Phe Ala Val Tyr Tyr Cys His Gln Ser Ser Arg
            100                 105                 110

Leu Pro His Thr Phe Gly Gln Gly Thr Lys Val Glu Ile Lys Arg Thr
        115                 120                 125


<210> SEQ ID NO 9
<211> LENGTH: 137
<212> TYPE: PRT
<213> ORGANISM: Homo sapiens

<400> SEQUENCE: 9

Met Glu Phe Gly Leu Ser Trp Val Phe Leu Val Ala Ile Leu Lys Gly
1               5                   10                  15

Val Gln Cys Glu Val Gln Leu Val Gln Ser Gly Gly Gly Leu Val Lys
            20                  25                  30

Pro Gly Gly Ser Leu Arg Leu Ser Cys Ala Ala Ser Gly Phe Thr Phe
        35                  40                  45

Ser Ser Phe Ala Met His Trp Val Arg Gln Ala Pro Gly Lys Gly Leu
    50                  55                  60

Glu Trp Ile Ser Val Ile Asp Thr Arg Gly Ala Thr Tyr Tyr Ala Asp
65                  70                  75                  80

Ser Val Lys Gly Arg Phe Thr Ile Ser Arg Asp Asn Ala Lys Asn Ser
                85                  90                  95
```

```
Leu Tyr Leu Gln Met Asn Ser Leu Arg Ala Glu Asp Thr Ala Val Tyr
            100                 105                 110

Tyr Cys Ala Arg Leu Gly Asn Phe Tyr Tyr Gly Met Asp Val Trp Gly
        115                 120                 125

Gln Gly Thr Thr Val Thr Val Ser Ser
    130                 135


<210> SEQ ID NO 10
<211> LENGTH: 137
<212> TYPE: PRT
<213> ORGANISM: Homo sapiens

<400> SEQUENCE: 10

Met Glu Phe Gly Leu Ser Trp Val Phe Leu Val Ala Ile Leu Lys Gly
1               5                   10                  15

Val Gln Cys Glu Val Gln Leu Val Gln Ser Gly Gly Gly Leu Val Gln
            20                  25                  30

Pro Gly Gly Ser Leu Arg Leu Ser Cys Ala Ala Ser Gly Phe Thr Phe
        35                  40                  45

Ser Ser Phe Ala Met His Trp Val Arg Gln Ala Pro Gly Lys Gly Leu
    50                  55                  60

Glu Trp Ile Ser Val Ile Asp Thr Arg Gly Ala Thr Tyr Tyr Ala Asp
65                  70                  75                  80

Ser Val Lys Gly Arg Phe Thr Ile Ser Arg Asp Asn Ala Lys Asn Ser
                85                  90                  95

Leu Tyr Leu Gln Met Asn Ser Leu Arg Ala Glu Asp Thr Ala Val Tyr
            100                 105                 110

Tyr Cys Ala Arg Leu Gly Asn Phe Tyr Tyr Gly Met Asp Val Trp Gly
        115                 120                 125

Gln Gly Thr Thr Val Thr Val Ser Ser
    130                 135


<210> SEQ ID NO 11
<211> LENGTH: 219
<212> TYPE: PRT
<213> ORGANISM: Artificial Sequence
<220> FEATURE:
<223> OTHER INFORMATION: Light chain immunoglobulin

<400> SEQUENCE: 11

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Ile Val His Ser
            20                  25                  30

Asn Gly Asn Thr Tyr Leu Gln Trp Tyr Leu Gln Lys Pro Gly Gln Ser
        35                  40                  45

Pro Gln Leu Leu Ile Tyr Lys Val Ser Asn Arg Leu Tyr Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Val Pro Trp Thr Phe Gly Gln Gly Thr Lys Val Glu Ile Lys
            100                 105                 110

Arg Thr Val Ala Ala Pro Ser Val Phe Ile Phe Pro Pro Ser Asp Glu
        115                 120                 125
```

```
Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215


<210> SEQ ID NO 12
<211> LENGTH: 447
<212> TYPE: PRT
<213> ORGANISM: Artificial Sequence
<220> FEATURE:
<223> OTHER INFORMATION: Heavy chain immunoglobulin

<400> SEQUENCE: 12

Gln Val Gln Leu Gln Glu Ser Gly Pro Gly Leu Val Lys Pro Ser Glu
1               5                   10                  15

Thr Leu Ser Leu Thr Cys Thr Val Ser Gly Tyr Ser Ile Thr Gly Gly
            20                  25                  30

Tyr Leu Trp Asn Trp Ile Arg Gln Pro Pro Gly Lys Gly Leu Glu Trp
        35                  40                  45

Ile Gly Tyr Ile Ser Tyr Asp Gly Thr Asn Asn Tyr Lys Pro Ser Leu
    50                  55                  60

Lys Asp Arg Val Thr Ile Ser Arg Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Tyr Gly Arg Val Phe Phe Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Arg Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270
```

```
Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445


<210> SEQ ID NO 13
<211> LENGTH: 118
<212> TYPE: PRT
<213> ORGANISM: Artificial Sequence
<220> FEATURE:
<223> OTHER INFORMATION: Heavy chain immunoglobulin

<400> SEQUENCE: 13

Glu Val Gln Leu Gln Gln Ser Gly Ala Glu Leu Val Lys Pro Gly Ala
1               5                   10                  15

Ser Val Thr Leu Ser Cys Thr Ala Ser Gly Phe Asn Ile Lys Asp Thr
            20                  25                  30

Tyr Met His Trp Val Asn Gln Arg Pro Glu Gln Gly Leu Val Trp Ile
        35                  40                  45

Gly Arg Ile Asp Pro Ala Asn Gly His Thr Glu Tyr Asp Pro Lys Phe
    50                  55                  60

Gln Asp Lys Ala Thr Ile Thr Thr Asp Thr Ser Ser Asn Thr Ala Tyr
65                  70                  75                  80

Leu His Leu Ser Ser Leu Thr Ser Gly Asp Thr Ala Val Tyr Tyr Cys
                85                  90                  95

Ala Arg Ser Tyr Phe Gly Ser Ile Phe Ala Tyr Trp Gly Gln Gly Thr
            100                 105                 110

Leu Val Thr Val Ser Ala
        115


<210> SEQ ID NO 14
<211> LENGTH: 108
<212> TYPE: PRT
<213> ORGANISM: Artificial Sequence
<220> FEATURE:
<223> OTHER INFORMATION: Light chain immunoglobulin

<400> SEQUENCE: 14

Gln Ile Val Leu Thr Gln Ser Pro Ala Ile Met Ser Ala Ser Pro Gly
1               5                   10                  15
```

```
Glu Lys Val Thr Ile Ser Cys Ser Ala Ser Ser Ser Val Ser Tyr Leu
            20                  25                  30

Tyr Trp Tyr Gln Gln Lys Pro Gly Ser Ser Pro Lys Pro Trp Ile Phe
        35                  40                  45

Arg Ser Ser His Arg Ala Ser Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys His Gln Tyr Gln Ser Tyr Pro Pro Thr
                85                  90                  95

Phe Gly Gly Gly Thr Lys Leu Glu Ile Lys Arg Ala
            100                 105


<210> SEQ ID NO 15
<211> LENGTH: 118
<212> TYPE: PRT
<213> ORGANISM: Artificial Sequence
<220> FEATURE:
<223> OTHER INFORMATION: Heavy chain immunoglobulin

<400> SEQUENCE: 15

Glu Val Gln Leu Gln Gln Ser Gly Ala Asp Leu Val Lys Pro Gly Ala
1               5                   10                  15

Ser Val Lys Leu Ser Cys Thr Ala Ser Gly Phe Asn Ile Lys Asp Thr
            20                  25                  30

Tyr Ile His Trp Val Lys Gln Arg Pro Glu Gln Gly Leu Glu Trp Ile
        35                  40                  45

Gly Arg Ile Asp Pro Ala Asn Gly His Thr Glu Tyr Asp Pro Lys Phe
    50                  55                  60

Gln Gly Arg Ala Thr Leu Thr Thr Asp Thr Ser Ser Asn Thr Ala Tyr
65                  70                  75                  80

Leu Gln Leu Phe Ser Leu Thr Ser Glu Asp Ser Ala Val Tyr Phe Cys
                85                  90                  95

Ala Arg Ser Tyr Tyr Gly Ser Ile Phe Ala Tyr Trp Gly Gln Gly Thr
            100                 105                 110

Leu Val Thr Val Ser Ala
        115


<210> SEQ ID NO 16
<211> LENGTH: 108
<212> TYPE: PRT
<213> ORGANISM: Artificial Sequence
<220> FEATURE:
<223> OTHER INFORMATION: Light chain immunoglobulin

<400> SEQUENCE: 16

Gln Ile Val Leu Thr Gln Ser Pro Ala Ile Met Ser Ala Ser Pro Gly
1               5                   10                  15

Glu Lys Val Thr Ile Ser Cys Ser Ala Ser Ser Ser Val Ser Tyr Leu
            20                  25                  30

Phe Trp Tyr Gln Gln Lys Pro Gly Ser Ser Pro Lys Pro Trp Ile Phe
        35                  40                  45

Arg Thr Ser Tyr Leu Ala Ser Gly Val Pro Ala Arg Phe Ser Gly Ser
    50                  55                  60

Gly Ser Gly Thr Ser Phe Ser Leu Thr Ile Ser Ser Met Glu Ala Glu
65                  70                  75                  80

Asp Ala Ala Thr Tyr Tyr Cys His Gln Tyr His Thr Tyr Pro Pro Thr
```

```
                85                  90                  95

Phe Gly Gly Gly Thr Lys Leu Glu Ile Lys Arg Ala
            100                 105


<210> SEQ ID NO 17
<211> LENGTH: 121
<212> TYPE: PRT
<213> ORGANISM: Artificial Sequence
<220> FEATURE:
<223> OTHER INFORMATION: Heavy chain immunoglobulin

<400> SEQUENCE: 17

Glu Val Gln Leu Gln Gln Ser Gly Ala Glu Leu Val Arg Ser Gly Ala
1               5                   10                  15

Ser Val Lys Leu Ser Cys Thr Thr Ser Gly Phe Asn Ile Lys Asp Tyr
            20                  25                  30

Tyr Ile His Trp Val Lys Gln Arg Pro Glu Gln Gly Leu Glu Trp Ile
        35                  40                  45

Gly Trp Ile Asp Pro Glu Asn Gly Asp Thr Glu Tyr Ala Pro Lys Phe
    50                  55                  60

Gln Gly Lys Ala Thr Met Thr Ala Asp Thr Ser Ser Asn Thr Ala Tyr
65                  70                  75                  80

Leu Gln Leu Ser Ser Leu Thr Ser Ala Asp Thr Ala Val Tyr Tyr Cys
                85                  90                  95

Asn Ala Tyr Tyr Arg Tyr Asp Asp Gly Thr Trp Phe Pro Tyr Trp Gly
            100                 105                 110

Gln Gly Thr Leu Val Thr Val Ser Ala
        115                 120


<210> SEQ ID NO 18
<211> LENGTH: 109
<212> TYPE: PRT
<213> ORGANISM: Artificial Sequence
<220> FEATURE:
<223> OTHER INFORMATION: Light chain immunoglobulin

<400> SEQUENCE: 18

Asp Ile Gln Leu Thr Gln Ser Pro Ala Ser Leu Ser Ala Ser Val Gly
1               5                   10                  15

Glu Thr Val Thr Ile Thr Cys Arg Ala Ser Gly Asn Ile His Ser Tyr
            20                  25                  30

Leu Ala Trp Tyr Gln Gln Lys Gln Gly Lys Ser Pro Gln Phe Leu Val
        35                  40                  45

Asp Asn Ala Lys Thr Leu Pro Asp Gly Val Pro Ser Arg Phe Ser Val
    50                  55                  60

Ser Gly Ser Gly Thr Gln Tyr Ser Leu Lys Ile Asn Ser Leu Gln Pro
65                  70                  75                  80

Glu Asp Phe Gly Thr Tyr Tyr Cys Gln His Phe Trp Asn Thr Pro Trp
                85                  90                  95

Thr Phe Gly Gly Gly Thr Lys Leu Glu Ile Lys Arg Ala
            100                 105


<210> SEQ ID NO 19
<211> LENGTH: 119
<212> TYPE: PRT
<213> ORGANISM: Artificial Sequence
<220> FEATURE:
<223> OTHER INFORMATION: Heavy chain immunoglobulin

<400> SEQUENCE: 19
```

```
Glu Val Leu Leu Gln Gln Ser Val Ala Glu Leu Val Arg Pro Gly Ala
1               5                   10                  15

Ser Val Arg Leu Ser Cys Thr Ala Ser Gly Phe Asn Ile Lys Asp Thr
            20                  25                  30

Tyr Ile His Trp Val Arg Gln Arg Pro Glu Gln Gly Leu Glu Trp Phe
        35                  40                  45

Gly Trp Ile Asp Pro Ala Asn Gly Tyr Thr Lys Tyr Ala Pro Asn Phe
    50                  55                  60

Gln Gly Lys Ala Thr Leu Thr Thr Asp Thr Ser Ser Asn Thr Ala Tyr
65                  70                  75                  80

Leu His Leu Ser Ser Leu Thr Ser Glu Asp Ser Ala Ile Tyr Tyr Cys
                85                  90                  95

Ala Arg Gly Tyr Tyr Arg Tyr Tyr Ser Leu Asp Tyr Trp Gly Gln Gly
            100                 105                 110

Thr Ser Val Thr Val Ser Ser
        115


<210> SEQ ID NO 20
<211> LENGTH: 109
<212> TYPE: PRT
<213> ORGANISM: Artificial Sequence
<220> FEATURE:
<223> OTHER INFORMATION: Light chain immunoglobulin

<400> SEQUENCE: 20

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Asn Tyr
            20                  25                  30

Leu Asn Trp Tyr Gln Gln Lys Pro Asp Gly Thr Val Lys Leu Leu Ile
        35                  40                  45

Tyr Tyr Ser Ser Arg Leu His Ser Gly Val Pro Ser Arg Phe Ser Gly
    50                  55                  60

Arg Gly Ser Gly Thr Asp Tyr Ser Leu Thr Ile Ser Thr Leu Glu Gln
65                  70                  75                  80

Glu Asp Ile Ala Thr Tyr Phe Cys Gln Gln Gly Lys Thr Leu Pro Leu
                85                  90                  95

Thr Phe Gly Ala Gly Thr Lys Leu Glu Leu Lys Arg Ala
            100                 105


<210> SEQ ID NO 21
<211> LENGTH: 126
<212> TYPE: PRT
<213> ORGANISM: Artificial Sequence
<220> FEATURE:
<223> OTHER INFORMATION: Heavy chain immunoglobulin

<400> SEQUENCE: 21

Glu Val Gln Leu Val Asp Ser Gly Gly Gly Leu Val Gln Pro Gly Arg
1               5                   10                  15

Ser Leu Lys Leu Ser Cys Ala Ala Ser Gly Phe Thr Phe Ser Asn His
            20                  25                  30

Asp Met Ala Trp Val Arg Gln Ala Pro Thr Lys Gly Leu Glu Trp Val
        35                  40                  45

Ala Ser Ile Thr Pro Ser Gly Gly Thr Thr Tyr Tyr Arg Asp Ser Val
    50                  55                  60

Glu Gly Arg Phe Thr Val Ser Arg Asp Asn Val Lys Ser Ser Leu His
```

```
65                  70                  75                  80

Leu Gln Met Asp Ser Leu Thr Ser Glu Asp Thr Ala Thr Tyr Tyr Cys
                85                  90                  95

Ala Arg Gln Asn Tyr Tyr Asp Gly Ser Tyr Tyr Tyr Gly Leu Tyr Tyr
            100                 105                 110

Phe Asp Tyr Trp Gly Gln Gly Val Met Val Thr Val Ser Ser
        115                 120                 125


<210> SEQ ID NO 22
<211> LENGTH: 114
<212> TYPE: PRT
<213> ORGANISM: Artificial Sequence
<220> FEATURE:
<223> OTHER INFORMATION: Light chain immunoglobulin

<400> SEQUENCE: 22

Asp Val Leu Met Thr Gln Thr Pro Val Ser Leu Pro Val Ser Leu Gly
1               5                   10                  15

Gly Gln Val Ser Ile Ser Cys Arg Ser Ser Gln Ser Leu Val Tyr Ser
            20                  25                  30

Asp Gly Asn Thr Tyr Leu His Trp Tyr Leu Gln Lys Pro Gly Gln Ser
        35                  40                  45

Pro Gln Leu Leu Ile Tyr Arg Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Pro Glu Asp Leu Gly Leu Tyr Tyr Cys Leu Gln Ser
                85                  90                  95

Thr His Phe Pro Pro Thr Phe Gly Ser Gly Thr Lys Leu Glu Ile Lys
            100                 105                 110

Arg Ala


<210> SEQ ID NO 23
<211> LENGTH: 119
<212> TYPE: PRT
<213> ORGANISM: Artificial Sequence
<220> FEATURE:
<223> OTHER INFORMATION: Heavy chain immunoglobulin

<400> SEQUENCE: 23

Glu Val Gln Leu Gln Gln Ser Gly Pro Glu Leu Val Lys Pro Gly Ala
1               5                   10                  15

Ser Val Lys Ile Ser Cys Lys Val Ser Gly Tyr Thr Phe Thr Asp Tyr
            20                  25                  30

Tyr Met Asn Trp Val Lys Gln Ser His Gly Lys Ser Leu Glu Trp Ile
        35                  40                  45

Gly Asp Ile Asn Pro Asn Asn Gly Gly Ala Ile Tyr Asn Gln Lys Phe
    50                  55                  60

Lys Gly Lys Ala Thr Leu Thr Val Asp Lys Ser Ser Ser Ile Ala Tyr
65                  70                  75                  80

Met Glu Leu Arg Ser Leu Thr Ser Glu Asp Ser Ala Val Tyr Tyr Cys
                85                  90                  95

Thr Ser Gly Ile Ile Thr Glu Ile Ala Glu Asp Phe Trp Gly Gln Gly
            100                 105                 110

Thr Thr Leu Thr Val Ser Ser
        115
```

<210> SEQ ID NO 24
<211> LENGTH: 109
<212> TYPE: PRT
<213> ORGANISM: Artificial Sequence
<220> FEATURE:
<223> OTHER INFORMATION: Light chain immunoglobulin

<400> SEQUENCE: 24

```
Asp Ile Val Met Thr Gln Ser Gln Lys Phe Met Ser Thr Ser Val Gly
1               5                   10                  15

Asp Arg Val Ser Val Thr Cys Lys Ala Ser Gln Asn Val Gly Thr Asn
            20                  25                  30

Val Val Trp Tyr Gln Gln Lys Pro Gly Gln Ser Pro Lys Ala Leu Ile
        35                  40                  45

His Ser Ala Ser Tyr Arg Tyr Ser Gly Val Pro Asp Arg Phe Lys Gly
    50                  55                  60

Ser Gly Ser Gly Thr Asp Phe Thr Leu Thr Ile Thr Asn Val Gln Ser
65                  70                  75                  80

Glu Asp Leu Ala Gly Phe Phe Cys Gln Gln Tyr Lys Thr Tyr Pro Tyr
                85                  90                  95

Thr Phe Gly Gly Gly Thr Gln Leu Glu Ile Lys Arg Ala
            100                 105
```

<210> SEQ ID NO 25
<211> LENGTH: 7328
<212> TYPE: DNA
<213> ORGANISM: Artificial Sequence
<220> FEATURE:
<223> OTHER INFORMATION: pAIL17L plasmid sequence

<400> SEQUENCE: 25

```
gcactataca tcaaatattc cttattaacc cctttacaaa ttaaaaagct aaaggtacac      60

aatttttgag catagttatt aatagcagac actctatgcc tgtgtggagt aagaaaaaac     120

agtatgttat gattataact gttatgccta cttataaagg ttacagaata tttttccata     180

attttcttgt atagcagtgc agctttttcc tttgtggtgt aaatagcaaa gcaagcaaga     240

gttctattac taaacacagc atgactcaaa aaacttagca attctgaagg aaagtccttg     300

gggtcttcta cctttctctt cttttttgga ggagtagaat gttgagagtc agcagtagcc     360

tcatcatcac tagatggcat ttcttctgag caaaacaggt tttcctcatt aaaggcattc     420

caccactgct cccattcatc agttccatag gttggaatct aaaatacaca aacaattaga     480

atcagtagtt taacacatta tacttaaa aatttatat ttaccttaga gctttaaatc     540

tctgtaggta gtttgtccaa ttatgtcaca ccacagaagt aaggttcctt cacaaagatc     600

gatctaaagc cagcaaaagt cccatggtct tataaaaatg catagcttta ggaggggagc     660

agagaacttg aaagcatctt cctgttagtc tttcttctcg tagacttcaa acttatactt     720

gatgcctttt tcctcctgga cctcagagag gacgcctggg tattctggga gaagtttata     780

tttccccaaa tcaatttctg ggaaaaacgt gtcactttca aattcctgca tgatccttgt     840

cacaaagagt ctgaggtggc ctggttgatt catggcttcc tggtaaacag aactgcctcc     900

gactatccaa accatgtcta ctttacttgc caattccggt tgttcaataa gtcttaaggc     960

atcatccaaa cttttggcaa gaaaatgagc tcctcgtggt ggttctttga gttctctact    1020

gagaactata ttaattctgt cctttaaagg tcgattcttc tcaggaatgg agaaccaggt    1080

tttcctaccc ataatcacca gattctgttt accttccact gaagaggttg tggtcattct    1140

ttggaagtac ttgaactcgt tcctgagcgg aggccagggt aggtctccgt tcttgccaat    1200
```

```
ccccatattt tgggacacgg cgacgatgca gttcaatggt cgaaccatga tggcagcggg   1260
gataaaatcc taccagcctt cacgctagga ttgccgtcaa gtttggcgcg aaatcgcagc   1320
cctgagctgt cccccccccc aagctcagat ctgagcttgg tccctatggt gagtccgttc   1380
cgctcttgtg atgatagcca gacaagaaag agacaataca agacaaacac caaatagtag   1440
aaatagagac aagggtcact tatccgaggg tccctgttcg ggcgccagct gccgcagtcg   1500
gccgacctga gggtcgccgg ggtctgcggg gggaccctct ggaaagtgaa ggataagtga   1560
cgagcggaga cgggatggcg aacagacaca aacacacaag aggtgaatgt taggactgtt   1620
gcaagtttac tcaaaaaatc agcactcttt tatatcttgg tttacataag catttacata   1680
agatttggat aaattccaaa agaacatagg aaaatagaac actcagagct cagatcagaa   1740
cctttgatac caaaccaagt caggaaacca cttgtctcac atcctcgttt taagaacagt   1800
ttgtaaccaa aaacttactt aagccctggg aaccgcaagg ttgggccaat aaaggctatt   1860
cataataact catgccatga gtttttgcag aataatgttc tattagtcca gccactgtcc   1920
cctccttggt atggaaaatc tttccccaaa agtgcattcc tgttcctaga taaatataat   1980
catgtacctg ttgtttcatg tcgtcttttt cttcttgaga caacatacac caaggaggtc   2040
tagctctggc gagtctttca cgaaaaggga gggatctata taacacttta tagccattga   2100
ctgtaaccca cctatcccaa tttaagtcat atcttcctgt atatggtaag gggcatctg    2160
ttggtctgta gatgtaaggt cccctataag tccctggttg ccaccacctg tctcctattt   2220
tgacaaaaac actctttttt ccctttttta cttctaggcc tgtggtcaat agtccttgca   2280
cctgttcttc aattgaggtt gagcgtctct ttctattttc tattcccatt tctaacttct   2340
gaatttgagt aaaaatagta ctaaaagata atgattcatt tcttaacata gtaactaata   2400
atctacctat tggattggtc ttattggtaa aaatataatt tttagcaagc attcttattt   2460
ctatttctga aggacaaaat cgatgcggct tgtaagagga agttggctgt ggtccttgcc   2520
tcaggaggaa ggtcgagttc tccgaattgt ttagattgta atcttgcaca gaagagctat   2580
taaaagagtc aagggtgaga gccctgcgag cacgaaccgc aacttccccc aatagcccca   2640
ggcaaagcag agctatgcca agtttgcagc agagaatgaa tatgtctttg tctgatgggc   2700
tcatccgttt gtgcgcagac gggtcgtcct tggtgggaaa caaccccttg gctgcttctc   2760
ccctaggtgt aggacactct cgggagttca accatttctg cccaagctca gatctgagct   2820
ttaatgcggt agtttatcac agttaaattg ctaacgcagt caggcaccgt gtatgaaatc   2880
taacaatgcg ctcatcgtca tcctcggcac cgtcaccctg gatgctgtag gcataggctt   2940
ggttatgccg gtactgccgg gcctcttgcg ggatatcgtc cattccgaca gcatcgccag   3000
tcactatggc gtgctgctag cgctcttccg cttcctcgct cactgactcg ctgcgctcgg   3060
tcgttcggct gcggcgagcg gtatcagctc actcaaaggc ggtaatacgg ttatccacag   3120
aatcagggga taacgcagga aagaacatgt gagcaaaagg ccagcaaaag gccaggaacc   3180
gtaaaaaggc cgcgttgctg gcgtttttcc ataggctccg cccccctgac gagcatcaca   3240
aaaatcgacg ctcaagtcag aggtggcgaa acccgacagg actataaaga taccaggcgt   3300
ttccccctgg aagctccctc gtgcgctctc ctgttccgac cctgccgctt accggatacc   3360
tgtccgcctt tctcccttcg ggaagcgtgg cgctttctca tagctcacgc tgtaggtatc   3420
tcagttcggt gtaggtcgtt cgctccaagc tgggctgtgt gcacgaaccc cccgttcagc   3480
ccgaccgctg cgccttatcc ggtaactatc gtcttgagtc caacccggta agacacgact   3540
```

```
tatcgccact ggcagcagcc actggtaaca ggattagcag agcgaggtat gtaggcggtg   3600
ctacagagtt cttgaagtgg tggcctaact acggctacac tagaaggaca gtatttggta   3660
tctgcgctct gctgaagcca gttaccttcg gaaaaagagt tggtagctct tgatccggca   3720
aacaaaccac cgctggtagc ggtggttttt ttgtttgcaa gcagcagatt acgcgcagaa   3780
aaaaaggatc tcaagaagat cctttgatct tttctacggg gtctgacgct cagtggaacg   3840
aaaactcacg ttaagggatt ttggtcatga gattatcaaa aaggatcttc acctagatcc   3900
ttttaaatta aaaatgaagt tttaaatcaa tctaaagtat atatgagtaa acttggtctg   3960
acagttacca atgcttaatc agtgaggcac ctatctcagc gatctgtcta tttcgttcat   4020
ccatagttgc ctgactcccc gtcgtgtaga taactacgat acgggagggc ttaccatctg   4080
gccccagtgc tgcaatgata ccgcgagacc cacgctcacc ggctccagat ttatcagcaa   4140
taaaccagcc agccggaagg gccgagcgca gaagtggtcc tgcaacttta tccgcctcca   4200
tccagtctat taattgttgc cgggaagcta gagtaagtag ttcgccagtt aatagtttgc   4260
gcaacgttgt tgccattgct acaggcatcg tggtgtcacg ctcgtcgttt ggtatggctt   4320
cattcagctc cggttcccaa cgatcaaggc gagttacatg atcccccatg ttgtgcaaaa   4380
aagcggttag ctccttcggt cctccgatcg ttgtcagaag taagttggcc gcagtgttat   4440
cactcatggt tatggcagca ctgcataatt ctcttactgt catgccatcc gtaagatgct   4500
tttctgtgac tggtgagtac tcaaccaagt cattctgaga atagtgtatg cggcgaccga   4560
gttgctcttg cccggcgtca acacgggata ataccgcgcc acatagcaga actttaaaag   4620
tgctcatcat tggaaaacgt tcttcggggc gaaaactctc aaggatctta ccgctgttga   4680
gatccagttc gatgtaaccc actcgtgcac ccaactgatc ttcagcatct tttactttca   4740
ccagcgtttc tgggtgagca aaaacaggaa ggcaaaatgc cgcaaaaaag ggaataaggg   4800
cgacacggaa atgttgaata ctcatactct tcctttttca atattattga agcatttatc   4860
agggttattg tctcatgagc ggatacatat ttgaatgtat ttagaaaaat aaacaaatag   4920
gggttccgcg cacatttccc cgaaaagtgc cacctgacgt ctaagagacc attattatca   4980
tgacattaac ctataaaaat aggcgtatca cgaggccctt tcgtcttcaa gaattgtcta   5040
gaggcgcgcc gtttaaaccc tcagctgatc atccggatgt acagcgcgcg gccggccggt   5100
accacgcgtt ggccacatat ggcggccgct cgcgattaat taatcgcgat ggccacatat   5160
ggagctctct agagcttgtc gacagatccc cctcttcatt tctttatgtt ttaaatgcac   5220
tgacctccca cattcccttt ttagtaaaat attcagaaat aatttaaata catcattgca   5280
atgaaaataa atgtttttta ttaggcagaa tccagatgct caaggccctt cataatatcc   5340
cccagtttag tagttggact tagggaacaa aggaaccttt aatagaaatt ggacagcaag   5400
aaagcgaggg ggatctggat cctccggagg gccccttctc cctctaacac tctcccctgt   5460
tgaagctctt tgtgacgggc gagctcaggc cctgatgggt gacttcgcag gcgtagactt   5520
tgtgtttctc gtagtctgct ttgctcagcg tcagggtgct gctgaggctg taggtgctgt   5580
ccttgctgtc ctgctctgtg acactctcct gggagttacc cgattggagg gcgttatcca   5640
ccttccactg tactttggcc tctctgggat agaagttatt cagcaggcac acaacagagg   5700
cagttccaga tttcaactgc tcatcagatg gcgggaagat gaagacagat ggtgcagcca   5760
ccgtacgttt gatttccacc ttggtcccct gtccaaaggt gtagggtgtg taatagctct   5820
gctgacagta gtacacgccc acatcttcgg cctccacccg gctgatcttc agagtgaaat   5880
ctgtcccaga tccgctgccg ctgaacctgt ctggcacccc gctctgccgg gtgctggtcc   5940
```

-continued

```
aatagatcag cagctgaggg ctctgccctg gtttctgcag ataccaggcc aggtagttct   6000

tctggttctc gctgaacagc aggctctggc tgctcttgca gctgatgctg gctggctctc   6060

cgggtgtcac aggcagggac agtggagact gggtcatcac gatatcacat ctcatggctg   6120

gcaggaacag caccagcagc cccagcagct gcactggagc catggtggcg gcgctagcga   6180

attcttaagc ctgtggagag aaaggaacag aaaacgaaac aaagacgtag agttgagcaa   6240

gcagggtcag gcaaagcgtg gagagccggc tgagtctagg taggctccaa gggagcgccg   6300

gacaaaggcc cggtctcgac ctgagcttta aacttacctg tggccacacg tgcaattgct   6360

atagtgagtc gtattaattt cgataagcca gtaagcagtg ggttctctag ttagccagag   6420

agctctgctt atatagacct cccaccgtac acgcctaccg cccatttgcg tcaatggggc   6480

ggagttgtta cgacattttg gaaagtcccg ttgattttgg tgccaaaaca aactcccatt   6540

gacgtcaatg gggtggagac ttggaaatcc ccgtgagtca aaccgctatc cacgcccatt   6600

gatgtactgc caaaaccgca tcaccatggt aatagcgatg actaatacgt agatgtactg   6660

ccaagtagga aagtcccata aggtcatgta ctgggcataa tgccaggcgg gccatttacc   6720

gtcattgacg tcaatagggg gcgtacttgg catatgatac acttgatgta ctgccaagtg   6780

ggcagtttac cgtaaatagt ccacccattg acgtcaatgg aaagtcccta ttggcgttac   6840

tatgggaaca tacgtcatta ttgacgtcaa tgggcggggg tcgttgggcg gtcagccagg   6900

cgggccattt accgtaagtt atgtaacgcg gaactccata tatgggctat gaactaatga   6960

ccccgtaatt gattactatt aataactagt caataatcaa tgtcaacgcg tatatctggc   7020

ccgtacatcg gtaactagtc ggaccggccc gggccaccgg tgctcgaagc ttggatcgat   7080

ccagacatga taagatacat tgatgagttt ggacaaacca caactagaat gcagtgaaaa   7140

aaatgcttta tttgtgaaat ttgtgatgct attgctttat ttgtaaccat tataagctgc   7200

aataaacaag ttaacaacaa caattgcatt cattttatgt ttcaggttca gggggaggtg   7260

tgggaggttt tttaaagcaa gtaaaacctc tacaaatgtg gtatggctga ttatgatctc   7320

tagtcaag                                                            7328
```